United States Patent
Zhou et al.

(10) Patent No.: US 7,514,431 B2
(45) Date of Patent: Apr. 7, 2009

(54) PIPERIDINYL CYCLOPENTYL ARYL BENZYLAMIDE MODULATORS OF CHEMOKINE RECEPTOR ACTIVITY

(75) Inventors: Changyou Zhou, Plainsboro, NJ (US); Alexander Pasternak, Princeton, NJ (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 104 days.

(21) Appl. No.: 10/533,337

(22) PCT Filed: Oct. 24, 2003

(86) PCT No.: PCT/US03/34099

§ 371 (c)(1),
(2), (4) Date: Mar. 30, 2006

(87) PCT Pub. No.: WO2004/041163

PCT Pub. Date: May 21, 2004

(65) Prior Publication Data

US 2006/0173013 A1    Aug. 3, 2006

Related U.S. Application Data

(60) Provisional application No. 60/422,381, filed on Oct. 30, 2002.

(51) Int. Cl.
| | | |
|---|---|---|
| *C07D 211/22* | (2006.01) | |
| *C07D 211/34* | (2006.01) | |
| *C07D 241/04* | (2006.01) | |
| *C07D 295/03* | (2006.01) | |
| *A61K 31/44* | (2006.01) | |
| *A61K 31/451* | (2006.01) | |
| *A61K 31/5375* | (2006.01) | |
| *A61P 29/00* | (2006.01) | |

(52) U.S. Cl. ............... 514/231.2; 514/252.12; 514/316; 546/191; 544/166; 544/358; 548/400

(58) Field of Classification Search .......... 546/191; 544/166, 358; 514/231.2, 252.12, 316, 212.01; 540/450, 484

See application file for complete search history.

(56) References Cited

U.S. PATENT DOCUMENTS

| | | |
|---|---|---|
| 2002/0049222 A1 | 4/2002 | Yang et al. |
| 2005/0250781 A1 | 11/2005 | Goble et al. |
| 2005/0250814 A1 | 11/2005 | Zhou et al. |
| 2005/0261325 A1 | 11/2005 | Butora et al. |
| 2006/0116421 A1 | 6/2006 | Butora et al. |

FOREIGN PATENT DOCUMENTS

GB    1486546    9/1977

OTHER PUBLICATIONS

Riberio et al. Pharmacology & therapeutics 107, 44-58, 2005.*
Onuffer et al., Trends in Pharmacological Sciences, 23(10), 459-467, 2002.*

* cited by examiner

*Primary Examiner*—Venkataraman Balasubramanian
(74) *Attorney, Agent, or Firm*—James L. McGinnis; Mark Daniel

(57) ABSTRACT

The present invention is directed to compounds of the formula I: I (wherein $R_1$, $R_2$, $R_3$, $R_4$, $R_5$, $R_6$, X, Z and n are defined herein) which are useful as modulators of chemokine receptor activity. In particular, these compounds are useful as modulators of the chemokine receptor CCR-2.

(I)

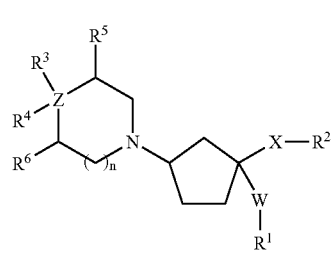

22 Claims, No Drawings

PIPERIDINYL CYCLOPENTYL ARYL BENZYLAMIDE MODULATORS OF CHEMOKINE RECEPTOR ACTIVITY

RELATED APPLICATION DATA

This is a National filing under 35 USC 371 of PCT/US2003/034099, filed Oct. 24, 2003, which claims priority from U.S. Ser. No. 60/422,381, filed Oct. 30, 2002.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165-183 (1991) and Murphy, *Rev. Immun.*, 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661-666 (1996)).

The chemokines are secreted by a wide variety of cell types and bind to specific G-protein coupled receptors (GPCRs) (reviewed in Horuk, *Trends Pharm. Sci.*, 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123-22128 (1995); Beote, et al, *Cell*, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908-928 (1997)); CCR-4 (or "CKR-4" or "CC-CKR-4") [MIP-1α, RANTES, MCP-1]-(Rollins, et al., *Blood*, 90, 908-928 (1997)); CCR-5 (or "CKR-5" or "CC-CKR-5") [MIP-1α, RANTES, MIP-1β] (Sanson, et al., *Biochemistry*, 35, 3362-3367 (1996)); and the Duffy blood-group antigen [RANTES, MCP-1] (Chaudhun, et al., *J. Biol. Chem.*, 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.*, 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., J. Exp. Med 187:601-608 (1998); Kurihara et al. J. Exp. Med. 186: 1757-1762 (1997); Boring et al. J. Clin. Invest. 100:2552-2561 (1997); Kuziel et al. Proc. Natl. Acad. Sci. 94:12053-12058 (1997)). Furthermore, these animals show reduced monocyte infiltration into granulomatous lesions induced by the injection of schistosomal or mycobacterial antigens (Boring et al. J. Clin. Invest. 100:2552-2561 (1997); Warmington et al. Am J. Path. 154:1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/− mice backcrossed to APO-E −/−, LDL-R −/− or Apo B transgenic mice maintained on high fat diets (Boring et al. Nature 394: 894-897 (1998); Gosling et al. J. Clin. Invest. 103:773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

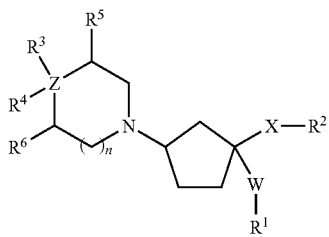

wherein:
X is selected from the group consisting of:
  $NR^{10}$—, —O—, —$CH_2O$—, —$CONR^{10}$—, —$NR^{10}CO$—, —$CO_2$—, —OCO—, —$CH_2(NR^{10})$CO—, —$N(COR^{10})$—, —$CH_2N(COR^{10})$—, phenyl, and $C_{3-6}$ cycloalkyl,
  where $R^{10}$ is independently selected from: hydrogen, $C_{1-6}$ alkyl, benzyl, phenyl, and $C_{1-6}$ alkyl-$C_{3-6}$ cycloalkyl, which is unsubstituted or substituted with 1-3 substituents where the substituents are independently selected from: halo, $C_{1-3}$alkyl, $C_{1-3}$alkoxy and trifluoromethyl;
W is selected from:
  phenyl and heterocycle, which is unsubstituted or substituted with 1-3 substituents where the substituents are independently selected from: halo, $C_{1-3}$alkoxy and trifluoromethyl;
Z is selected from:
  C, N, and —O—, wherein when Z is N, then $R^4$ is absent, and when W is —O—, then both $R^3$ and $R^4$ are absent;
n is an integer selected from 0, 1, 2, 3 and 4;
$R^1$ is selected from:
  (a) halo,
  (b) trifluoromethyl,
  (c) trifluoromethoxy,
  (d) hydroxy,
  (e) $C_{1-6}$alkyl,
  (f) $C_{3-7}$cycloalkyl,
  (g) —O—$C_{1-6}$alkyl,
  (h) —O—$C_{3-7}$cycloalkyl,
  (i) —$SCF_3$,
  (j) —S—$C_{1-6}$alkyl,
  (k) —$SO_2$—$C_{1-6}$alkyl,
  (l) phenyl,
  (m) heterocycle,
  (n) —$CO_2R^9$,
  (o) —CN,
  (p) —$NR^9R^{10}$,
  (q) —$NR^9$—$SO_2$—$R^{10}$,
  (r) —$SO_2$—$NR^9R^{10}$, and
  (s) —$CONR^9R^{10}$ (t) —NHC(=NE)$NH_2$, and
(u) hydrogen,
$R^2$ is selected from:
  ($C_{0-6}$alkyl)-phenyl and ($C_{0-6}$alkyl)-heterocycle,
    where the alkyl is unsubstituted or substituted with 1-7 substituents where the substituents are independently selected from:
    (a) halo,
    (b) hydroxy,
    (c) —O—$C_{1-3}$alkyl,
    (d) trifluoromethyl, and
    (e) —$C_{1-3}$alkyl,
    and where the phenyl and the heterocycle is unsubstituted or substituted with 1-5 substituents where the substituents are independently selected from:
    (a) halo,
    (b) trifluoromethyl,
    (c) trifluoromethoxy,
    (d) hydroxy,
    (e) $C_{1-6}$alkyl,
    (f) $C_{3-7}$cycloalkyl,
    (g) —O—$C_{1-6}$alkyl,
    (h) —O—$C_{3-7}$cycloalkyl,
    (i) —$SCF_3$,
    (j) —S—$C_{1-6}$alkyl,
    (k) —$SO_2$—$C_{1-6}$alkyl,
    (l) phenyl,
    (m) heterocycle,
    (n) —$CO_2R^9$,
    (o) —CN,
    (p) —$NR^9R^{10}$,
    (q) —$NR^9$—$SO_2$—$R^{10}$,
    (r) —$SO_2$—$NR^9R^{10}$, and
    (s) —$CONR^9R^{10}$;
$R^3$ is —($C_{0-6}$alkyl)-phenyl,
  where the alkyl is unsubstituted or substituted with 1-5 substituents where the substituents are independently selected from:
  (a) halo,
  (b) hydroxy,
  (c) —O—$C_{1-3}$alkyl, and
  (d) trifluoromethyl,
  and where the phenyl is unsubstituted or substituted with 1-5 substituents where the substituents are independently selected from:
  (a) halo,
  (b) trifluoromethyl,
  (c) hydroxy,
  (d) $C_{1-3}$alkyl,
  (e) —O—$C_{1-3}$alkyl,
  (f) —$CO_2R^9$,
  (g) —CN,
  (h) —$NR^9R^{10}$, and
  (i) —$CONR^9R^{10}$;
$R^4$ is selected from:
  (a) hydrogen,
  (b) hydroxy,
  (c) $C_{1-6}$alkyl,
  (d) $C_{1-6}$alkyl-hydroxy,
  (e) —O—$C_{1-3}$alkyl,
  (f) —$CO_2R^9$,
  (g) —$CONR^9R^{10}$, and
  (h) —CN;
or where $R^3$ and $R^4$ may be joined together to form a ring which is selected from:
  (a) 1H-indene,
  (b) 2,3-dihydro-1H-indene, (c) 2,3-dihydro-benzofuran,
(d) 1,3-dihydro-isobenzofuran,
(e) 2,3-dihydro-benzothiofuran, and
(f) 1,3-dihydro-isobenzothiofuran,
or where $R^3$ and $R^5$ or $R^4$ and $R^6$ may be joined together to form a ring which is phenyl,
  wherein the ring is unsubstituted or substituted with 1-7 substituents where the substituents are independently selected from:
    (a) halo,
    (b) trifluoromethyl,
    (c) hydroxy,
    (d) $C_{1-3}$alkyl,
    (e) —O—$C_{1-3}$alkyl,
    (f) —$CO_2R^9$,
    (g) —CN,
    (h) —$NR^9R^{10}$, and
    (i) —$CONR^9R^{10}$;
$R^5$ and $R^6$ are independently selected from:
  (a) hydrogen,
  (b) hydroxy,
  (c) $C_{1-6}$alkyl,
  (d) $C_{1-6}$alkyl-hydroxy,
  (e) —O—$C_{1-3}$alkyl,
  (f) oxo, and
  (g) halo;
and pharmaceutically acceptable salts thereof and individual diastereomers thereof.

Another embodiment of the present invention is directed to compounds of formula Ia:

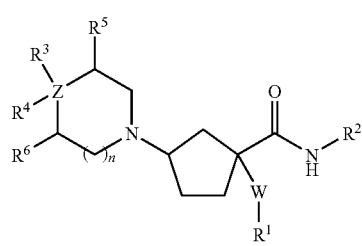

Ia wherein $R^1$, $R^2$, $R^3$, $R^3$, n, W and Z are defined herein;
and pharmaceutically acceptable salts and individual diastereomers thereof.

Another embodiment of the present invention is directed to compounds of formula Ib:

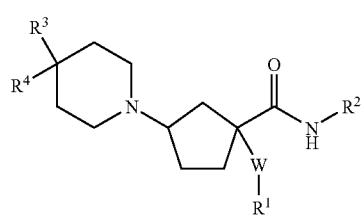

Ib wherein $R^1$, $R^2$, $R^3$, $R^4$, $R^5$, $R^6$, n and Z are defined herein;
and pharmaceutically acceptable salts and individual diastereomers thereof.

Another embodiment of the present invention is directed to compounds of formula Ic:

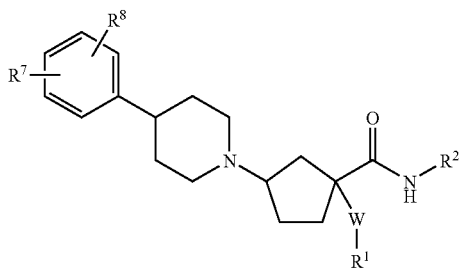

Ic wherein $R^1$, $R^2$ and W are defined herein,
and wherein $R^7$ and $R^8$ are independently selected from:
  (a) hydrogen,
  (b) halo,
  (c) trifluoromethyl,
  (d) hydroxy,
  (e) $C_{1-3}$alkyl,
  (f) —O—$C_{1-3}$alkyl,
  (g) —$CO_2H$,
  (h) —$CO_2C_{1-3}$alkyl, and
  (i) —CN;

and pharmaceutically acceptable salts and individual diastereomers thereof.

Another embodiment of the present invention is directed to compounds of formula Id:

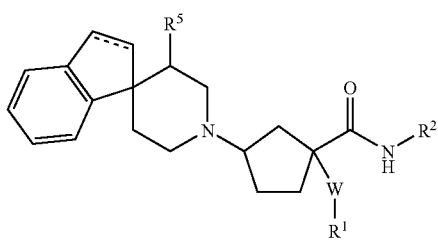

Id wherein the dash line represents either single or double bonds and $R^1$, $R^2$, $R^5$ are defined herein.

and pharmaceutically acceptable salts and individual diastereomers thereof.

Another embodiment of the present invention is directed to compounds wherein W is furanyl, imidazolyl, oxadiazolyl, oxazolyl, phenyl, pyrazolyl, pyrazinyl, pyridyl, pyridazinyl, pyrimidyl, pyrrolyl, thiadiazolyl, thiazolyl, thienyl, and triazolyl, and N-oxides thereof.

In the present invention it is most preferred that X is —CONH—.

In the present invention it is most preferred that Z is —C—, —N— or —O—.

In the present invention it is most preferred that n is 0 and 1.

In the present invention it is more preferred that $R^1$ is selected from:
  (a) hydrogen
  (b) halo
  (c) $C_{1-3}$alkyl,
  (d) —O—$C_{1-3}$alkyl,
  (e) —$CO_2R^9$, (f) —S—$C_{1-3}$alkyl,
(g) —$SO_2$—$C_{1-3}$alkyl,
(h) —$SCF_3$,
(i) NHC(=NH)$NR^9R^{10}$
(j) —$NR^9R^{10}$,
(k) —$NR^9$—$SO_2$—$R^{10}$,
(l) —$SO_2$—$NR^9R^{10}$, and
(m) —$CONR^9R^{10}$.

In the present invention it is preferred that $R^2$ is selected from —($C_{0-4}$alkyl)-phenyl and —($C_{0-4}$alkyl)-heterocycle,
where heterocycle is selected from:
furanyl, imidazolyl, oxadiazolyl, oxazolyl, pyrazolyl, pyrazinyl, pyridyl, pyridazinyl, pyrimidyl, pyrrolyl, thiadiazolyl, thiazolyl, thienyl, and triazolyl, and N-oxides thereof,
where the alkyl is unsubstituted or substituted with 1-7 substituents where the substituents are independently selected from:
(a) halo,
(b) hydroxy,
(c) —O—$C_{1-3}$alkyl, and
(d) trifluoromethyl,
and where the phenyl or heterocycle is unsubstituted or substituted with 1-5 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-13}$alkyl,
(g) —$CO_2R^9$,
(h) —S—$C_{1-3}$alkyl,
(i) —$SO_2$—$C_{1-3}$alkyl,
(j) —$SCF_3$,
(k) —$CO_2R^9$,
(l) —$NR^9R^{10}$,
(m) —$NR^9$—$SO_2$—$R^{10}$,
(n) —$SO_2$—$NR^9R^{10}$, and
(o) —$CONR^9R^{10}$.

In the present invention it is more preferred that $R^2$ is selected from —($C_{0-4}$alkyl)-phenyl and —($C_{0-4}$alkyl)-heterocycle,
where heterocycle is selected from: pyridyl, pyridazinyl, and N-oxides thereof,
where the alkyl is unsubstituted or substituted with 1-7 substituents where the substituents are independently selected from:
(a) halo,
(b) hydroxy,
(c) —O—$C_{1-3}$alkyl, and
(d) trifluoromethyl,
and where the phenyl or heterocycle is unsubstituted or substituted with 1-3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2H$,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

In the present invention it is even more preferred that $R^2$ is selected from —$CH_2$-phenyl and —$CH_2$-heterocycle,
where heterocycle is selected from: pyridyl, pyridazinyl, and N-oxides thereof,
and where the phenyl or heterocycle is unsubstituted or substituted with 1-3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2H$,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

In the present invention it is still more preferred that $R^2$ is selected from:
(1) —$CH_2$-(phenyl),
(2) —$CH_2$-(4-bromophenyl),
(3) —$CH_2$-(3-chlorophenyl),
(4) —$CH_2$-(3,5-difluorophenyl),
(5) —$CH_2$-((2-trifluoromethyl)phenyl),
(6) —$CH_2$-((3-trifluoromethyl)phenyl),
(7) —$CH_2$-((4-trifluoromethyl)phenyl),
(8) —$CH_2$-((3-trifluoromethoxy)phenyl),
(9) —$CH_2$-((3-trifluoromethylthio)phenyl),
(10) —$CH_2$-((3-trifluoromethoxy-5-thiomethyl)phenyl),
(11) —$CH_2$-((3-trifluoromethoxy-5-methoxy)phenyl),
(12) —$CH_2$-((3-trifluoromethoxy-5-methanesulfonyl)phenyl),
(13) —$CH_2$-((3-trifluoromethoxy-5-amino)phenyl),
(14) —$CH_2$-((3-trifluoromethoxy-5-aminomethanesulfonyl)phenyl),
(15) —$CH_2$-((3-trifluoromethoxy-5-sulfonylamino)phenyl),
(16) —$CH_2$-((3,5-bis-trifluoromethyl)phenyl),
(17) —$CH_2$-((3-fluoro-5-trifluoromethyl)phenyl),
(18) —CH($CH_3$)-((3,5-bis-trifluoromethyl)phenyl),
(19) —C($CH_3$)$_2$-((3,5-bis-trifluoromethyl)phenyl),
(20) —$CH_2$-(4-(2-trifluoromethyl)pyridyl),
(21) —$CH_2$-(5-(3-trifluoromethyl)pyridyl),
(22) —$CH_2$-(5-(3-trifluoromethyl)pyridazinyl),
(23) —$CH_2$-(4-(2-trifluoromethyl)pyridyl-N-oxide), and
(24) —$CH_2$-(5-(3-trifluoromethyl)pyridyl-N-oxide).

In the present invention it is preferred that $R^3$ is hydrogen or phenyl,
where the phenyl is unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$CO_2R^9$,
(g) —CN,
(h) —$NR^9R^{10}$, and
(i) —$CONR^9R^{10}$.

In the present invention it is more preferred that $R^3$ is hydrogen or phenyl, where the phenyl is unsubstituted or substituted with 1-3 substituents where the substituents are independently selected from:
(a) halo,
(c) hydroxy,
(d) $C_{1-3}$alkyl,
(e) —O—$C_{1-3}$alkyl, and
(f) —$CO_2R^9$.

In the present invention it is still more preferred that $R^3$ is phenyl, or para-fluorophenyl.

In the present invention it is more preferred that $R^4$ is selected from:
(a) hydrogen,
(b) hydroxy,
(c) —$CO_2H$,
(d) —$CO_2C_{1-6}$alkyl,
(e) —CN.

In the present invention it is more preferred that $R^5$ and $R^6$ are independently selected from:
(a) hydrogen,
(b) hydroxy,
(c) —$CH_3$,
(d) —O—$CH_3$, and
(e) oxo.

Especially preferred compounds of the present invention include those of the formula:

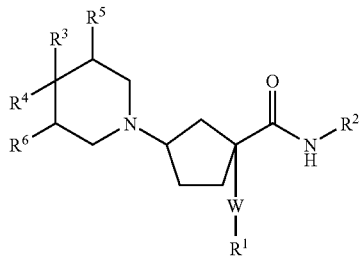

wherein W is selected from a furanyl, imidazolyl, oxadiazolyl, oxazolyl, phenyl, pyrazolyl, pyrazinyl, pyridyl, pyridazinyl, pyrimidyl, pyrrolyl, thiadiazolyl, thiazolyl, thienyl, or triazolyl ring, and $R^1$, $R^2$, $R^3$, $R^4$, $R^5$, $R^6$ are defined herein;

and pharmaceutically acceptable salts and individual diastereomers thereof.

The compounds of the instant invention have at two asymmetric centers at the amino acid part. Each such asymmetric center will independently produce two optical isomers and it is intended that all of the possible optical isomers and diastereomers in mixtures and as pure or partially purified compounds are included within the ambit of this invention. The absolute configurations of the most preferred compounds of this invention are those of the orientation as depicted:

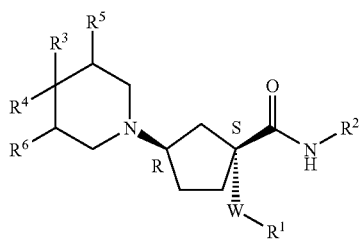

wherein the amide substituent is designated as being of the "S" absolute configuration (although the designation for the X substituent may be specified as "R" if the priority for assignment of the groups at that position differs) and the piperidine substituent is designated as being of "R" absolute configuration.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-bityl, tert-butyl, pentyl, hexyl, heptyl and octyl. Likewise, $C_0$, as in $C_0$allyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of 125I-MCP-1 to the endogenous CCR-2 receptor on various cell types including monocytes, THP-1 cells, or after heterologous expression of the cloned receptor in eukaryotic cells. The cells were suspended in binding buffer (50 mM Hepes, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM Hepes buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 µM Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells)-were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or MD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis, Hookworm, Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in the prevention and treatment of a wide variety of inflammatory and immunoregulatory disorders and diseases, allergic conditions, atopic conditions, as well as autoimmune pathologies. In a specific embodiment, the present invention is directed to the use of the subject compounds for the prevention or treatment of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in the prevention or treatment of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VIA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac; ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

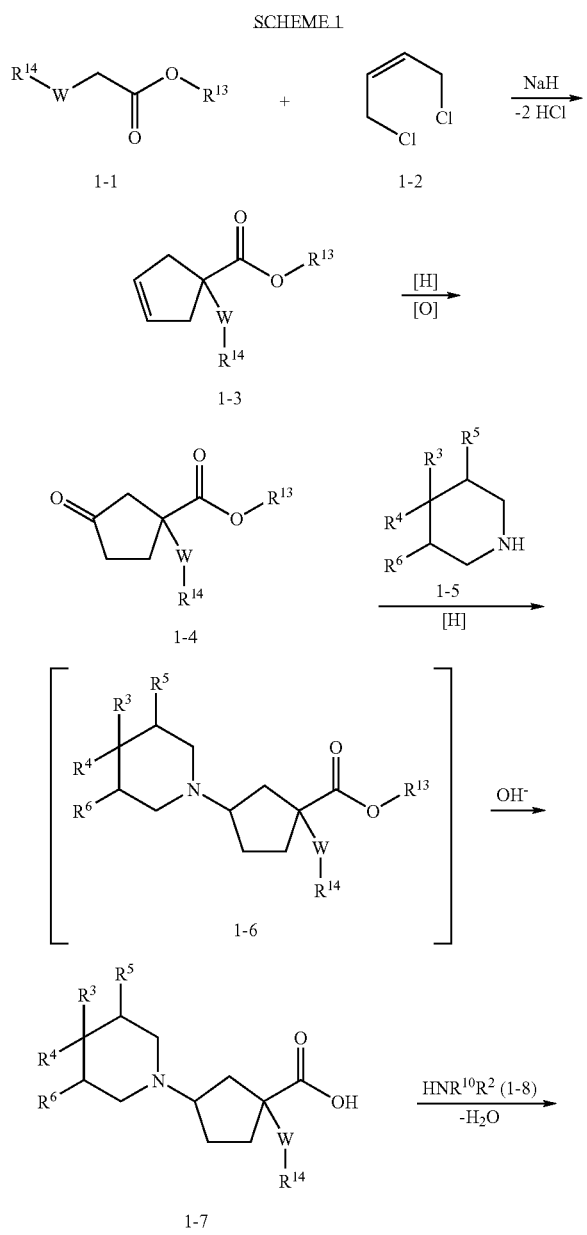

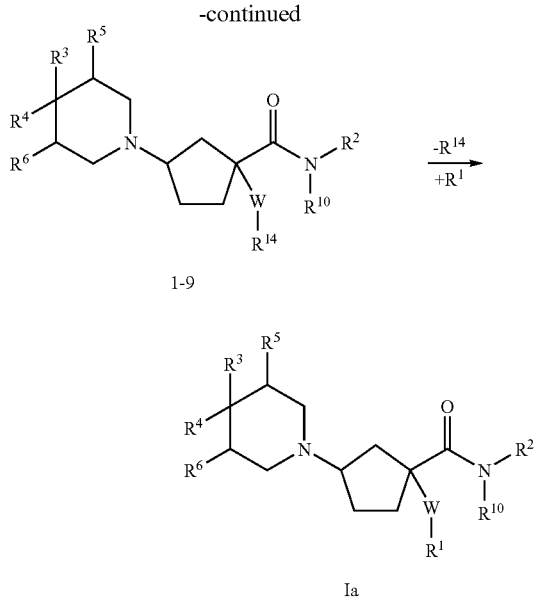

The preparation of compounds within the scope of the instant invention which bear a cyclopentane framework is detailed in Scheme 1.

The intermediate 1-3 can be synthesized by a ring-forming reaction, in which the substituted acetic ester 1-1 is dialkylated with cis-1,4-dichloro-2-butene 1-2 using a strong base such as sodium hydride, sodium, lithium or potassium hexamethyl-disilazide, lithium diisopropylamide, and the like in an appropriate solvent such as DMF, DMPU, DME or a mixture of them (Depres, J.-P.; Greene, A. E. J. Org. Chem. 1984, 49, 928-931).

Hydroboration of olefin 1-3, followed by oxidation with PCC affords the ketone 1-4. The ketone 1-4 could be reductively aminated with amine 1-5 to form the amino ester 1-6 under a variety of conditions, including sodium triacetoxyborohydride or sodium cyanoborohydride. The intermediate esters 1-6, formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 1-6 were hydrolytically cleaved to yield the respective acids 1-7. This hydrolysis was readily accomplished under usual conditions, including lithium, sodium or potassium hydroxide, at ambient to elevated temperatures, depending on the nature of the ester group and substituent $R^1$. These diastereoisomers could be separated by flash chromatography or crystallization from a variety of solvents taking advantage of the finding, that the cis-diastereoisomeric acids are less soluble, when compared to their trans-epimers.

The compounds of formula 1-9 are then formed from the acids 1-7 and amines 1-8 under standard amide-bond forming reaction conditions, including carbodiimide reagents, such as DCC, EDC and catalysts such as DMAP, HOAT or HOBT. After removal of the protecting group, the functional group can be further introduced onto the phenyl or heterocycle.

SCHEME 1A

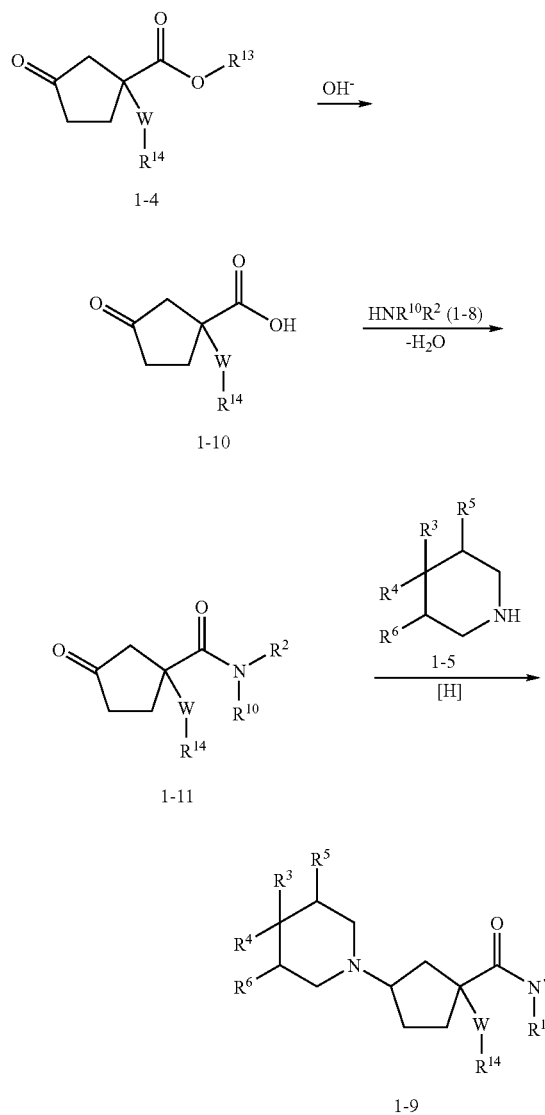

SCHEME 2

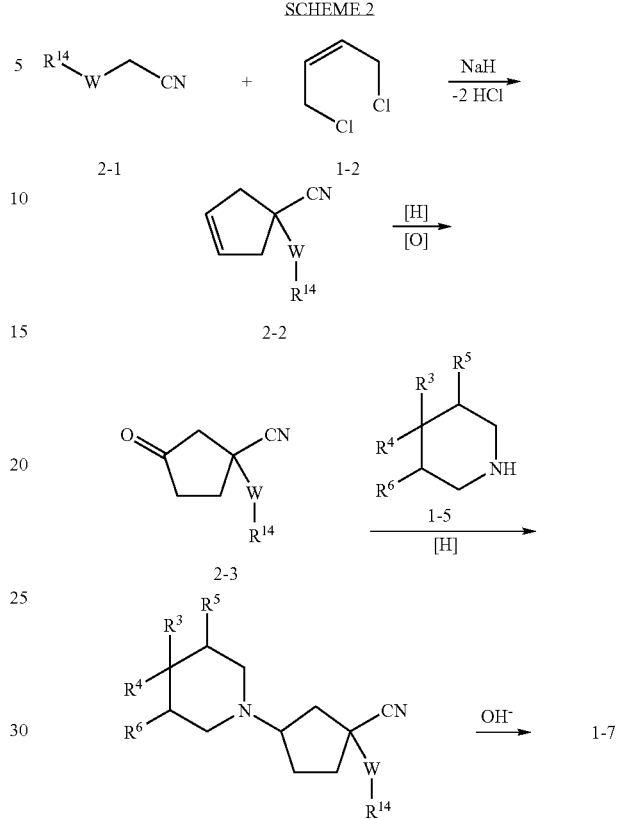

The keto esters 1-4 could in turn be transformed into the carboxylic acids 1-10 by a number of conditions depending on the nature of the ester. For example, methyl or ethyl esters can be readily saponified with sodium hydroxide, or lithium hydroxide; benzyl ester can be cleaved through palladium catalyzed hydrogenolysis; tert-butyl ester can be removed by treatment with TFA. The acids 1-10 were coupled with amines 1-8 as described above to form Intermediates 1-11. Transformation of 1-11 to the compound of the formula 1-9 can be achieved by reductive amination reaction conditions as described in Scheme 1. The compounds of the formula 1-9, formed in the above mentioned transformations represent in general a mixture of 1,3-cis- and 1,3-trans-diastereoisomers, which could be separated into respective diastereoisomeric pairs using column chromatography. 1,3-cis- or 1,3-trans-diastereoisomers can then further separated into their corresponding enantiomers.

The intermediate 1-7 can also be prepared from the nitrites 2-1 following the procedure as depicted in the Scheme 2. The intermediate 2-2 can be synthesized by a ring-forming reaction, in which the substituted acetonitrile 2-1 is dialkylated with cis-1,4-dichloro-2-butene 1-2 using a strong base such as sodium hydride, sodium, lithium or potassium hexamethyl-disilazide, lithium diisopropylamide, and the like in an appropriate solvent such as DMF, DMPU, DME or a mixture of them (Depres, J.-P.; Greene, A. E. J. Org. Chem. 1984, 49, 928-931).

Hydroboration of olefin 2-2, followed by oxidation with PCC affords the ketone 2-3. The ketone 2-3 could be reductively aminated with amine 1-5 to form the amino nitrile 2-4 under a variety of conditions, including sodium triacetoxyborohydride or sodium cyanoborohydride. The intermediate nitrites 2-4, formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 24 were hydrolytically cleaved to yield the respective acids 1-7. This hydrolysis was readily accomplished under usual conditions, including lithium, sodium or potassium hydroxide, at ambient to elevated temperatures, depending on the nature of the ester group and substituent $R^1$. These diastereoisomers could be separated by flash chromatography or crystallization from a variety of solvents taking advantage of the finding, that the cis-diastereoisomeric acids are less soluble, when compared to their trans-epimers.

SCHEME 3

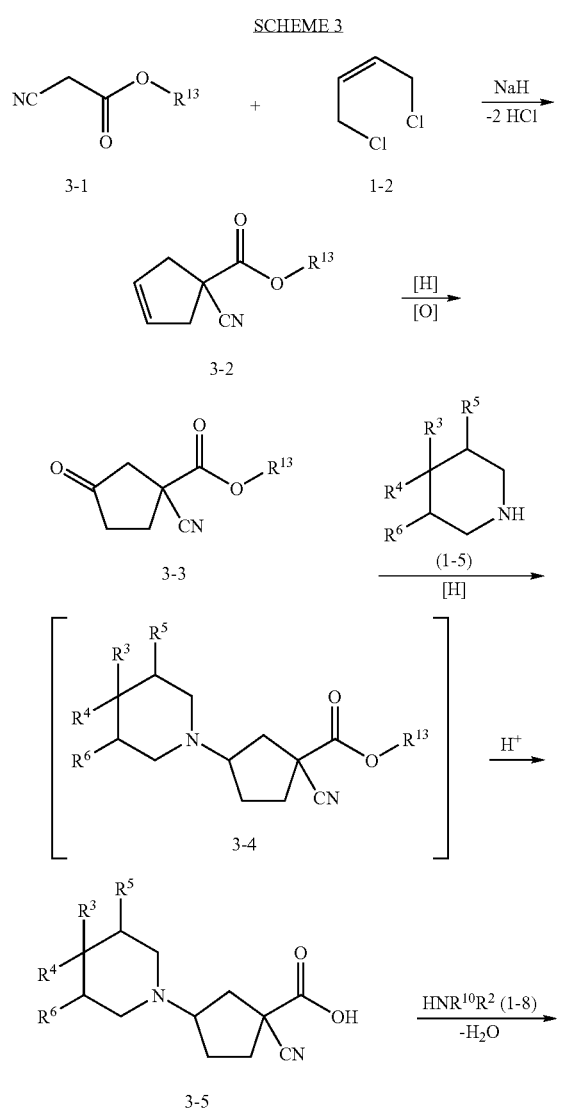

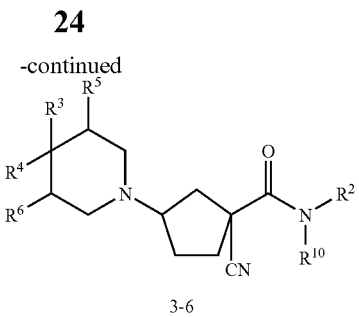

Heterocycles can be introduced at the later stage of the synthesis. The Scheme 3 depicts the synthesis of several key intermediates for the preparation of the heterocycles with special functionality.

The cyclization of α-cyano acetic ester 3-1 with cis-1,4-dichloro-2-butene 1-2 gives the ester 3-2 using a strong base such as sodium hydride, sodium, lithium or potassium hexamethyl-disilazide, lithium diisopropylamide, and the like in an appropriate solvent such as DMF, DMPU, DME or a mixture of them (Depres, J.-P.; Greene, A. E. J. Org. Chem. 1984, 49, 928-931).

Hydroboration of olefin 3-2, followed by oxidation with PCC affords the ketone 3-3 which could be reductively aminated with amine 1-5 to form the amino ester 3-4 under a variety of conditions, including sodium triacetoxyborohydride or sodium cyanoborohydride. The intermediate esters 3-4, formed in the above mentioned transformations represent in general a mixture of 1,3-cis- and 1,3-trans-diastereoisomers, which could be separated into respective diastereoisomeric pairs using column chromatography. A similar diastereoisomeric separation could be also accomplished later, after the esters 3-4 were hydrolytically cleaved to yield the respective acids 3-5. This selective hydrolysis was readily accomplished under usual conditions, including TFA and HCl at ambient to elevated temperatures. These diastereoisomers could be separated by flash chromatography or crystallization from a variety of solvents taking advantage of the finding, that the cis-diastereoisomeric acids are less soluble, when compared to their trans-epimers. The intermediate 3-6 are then formed from the acids 3-5 and amines 1-8 under standard amide-bond forming reaction conditions, including carbodiimide reagents, such as DCC, EDC and catalysts such as DMAP, HOAT or HOBT.

SCHEME 3A

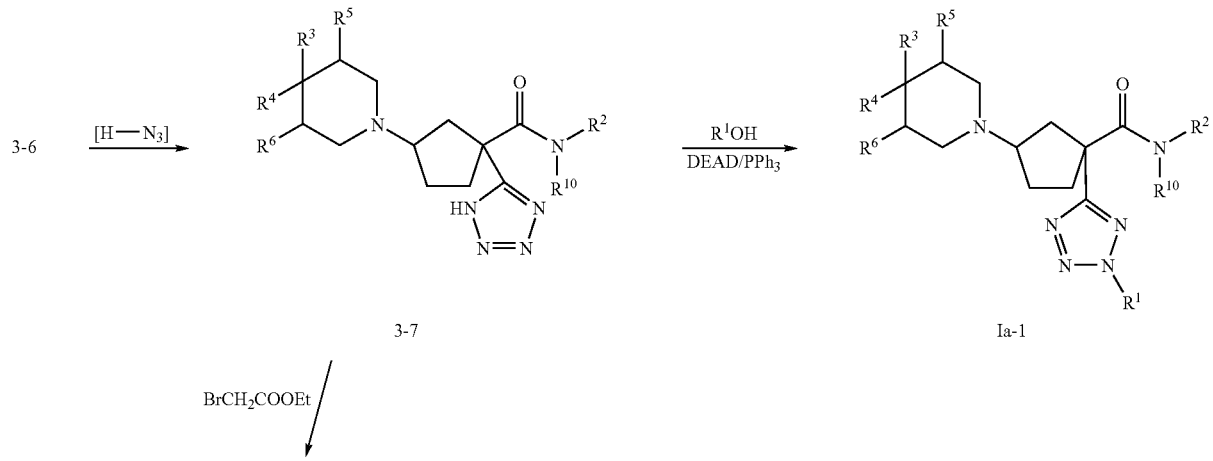

-continued
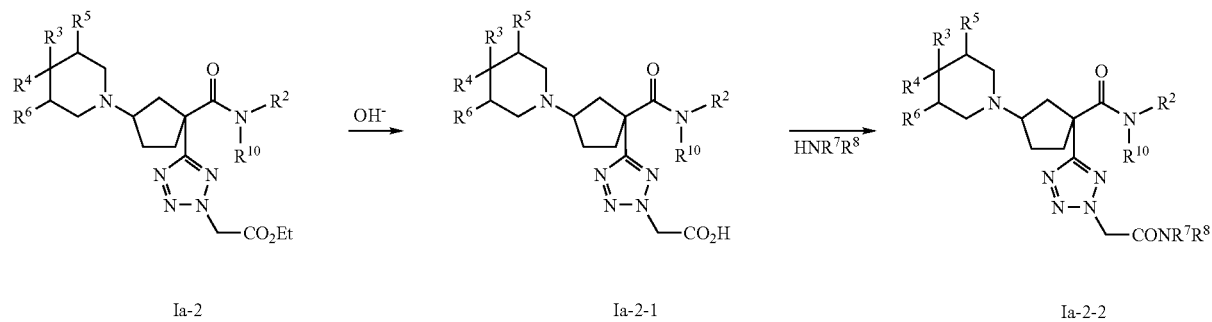
Ia-2    Ia-2-1    Ia-2-2
The amino nitrile 3-6 is converted into the tetrazole 3-7 by treatment with the azide. Further alkylation in the presence of base or under Mitsunobu's condition gives the alkylated tetrazole Ia-1 and Ia-2. The Ia-2 can also be converted into its acid Ia-2-1 or amide Ia-2-2 by hydrolysis and coupling under standard condition.
SCHEME 3B
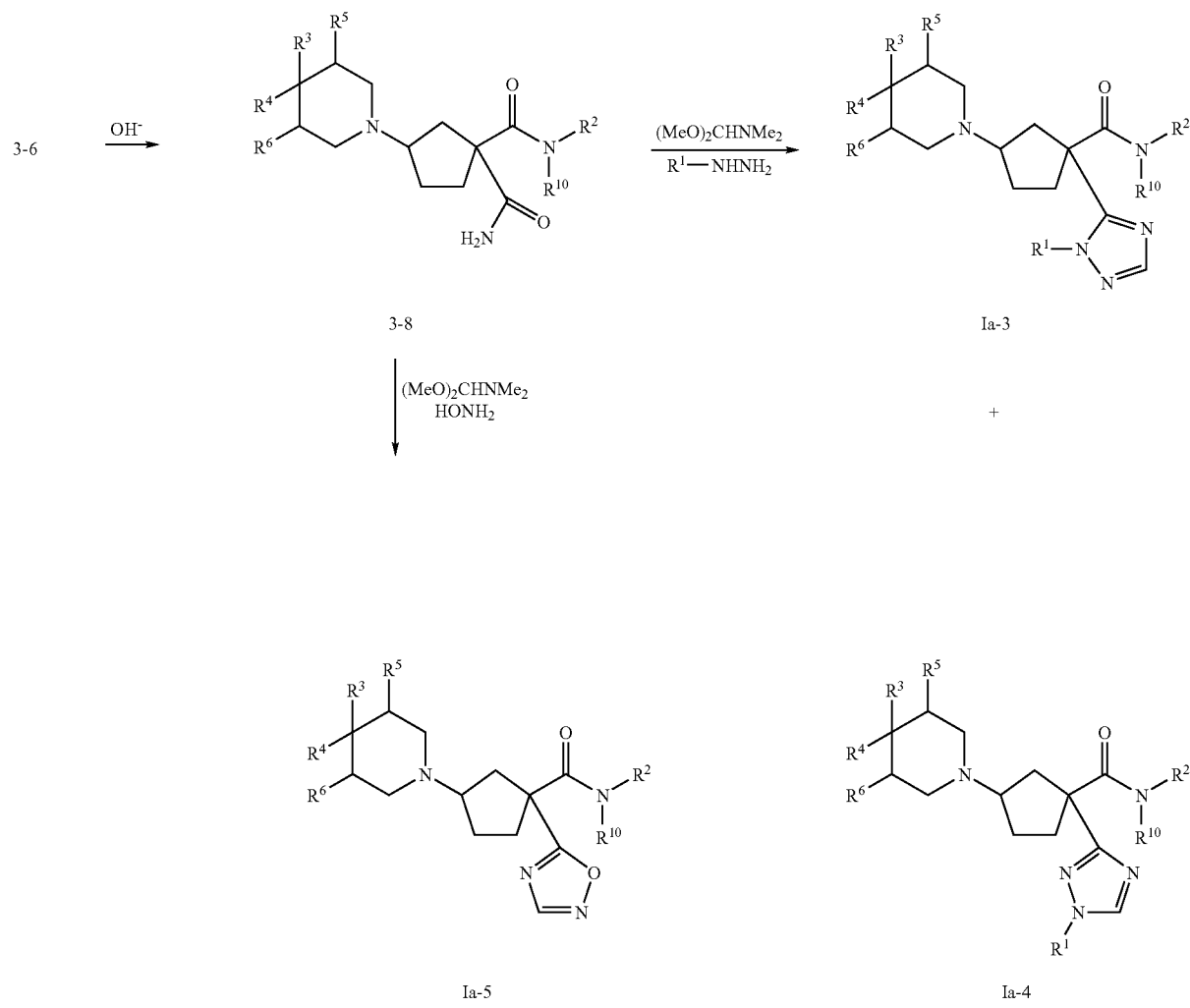

The hydrolysis of the nitriles 3-6 under basic condition give the amides 3-8 which can be converted the triazoles Ia-3 and Ia-4 as well as Ia-5 by treatment with (MeO)2CHNMe2 and hydrazine as well as hydroxyl amine.

followed by oxidation with PCC affords the ketone 4-6 which could be reductively aminated with amine 1-5 to form the amino ester 4-7 under a variety of conditions, including sodium triacetoxyborohydride or sodium cyanoborohydride.

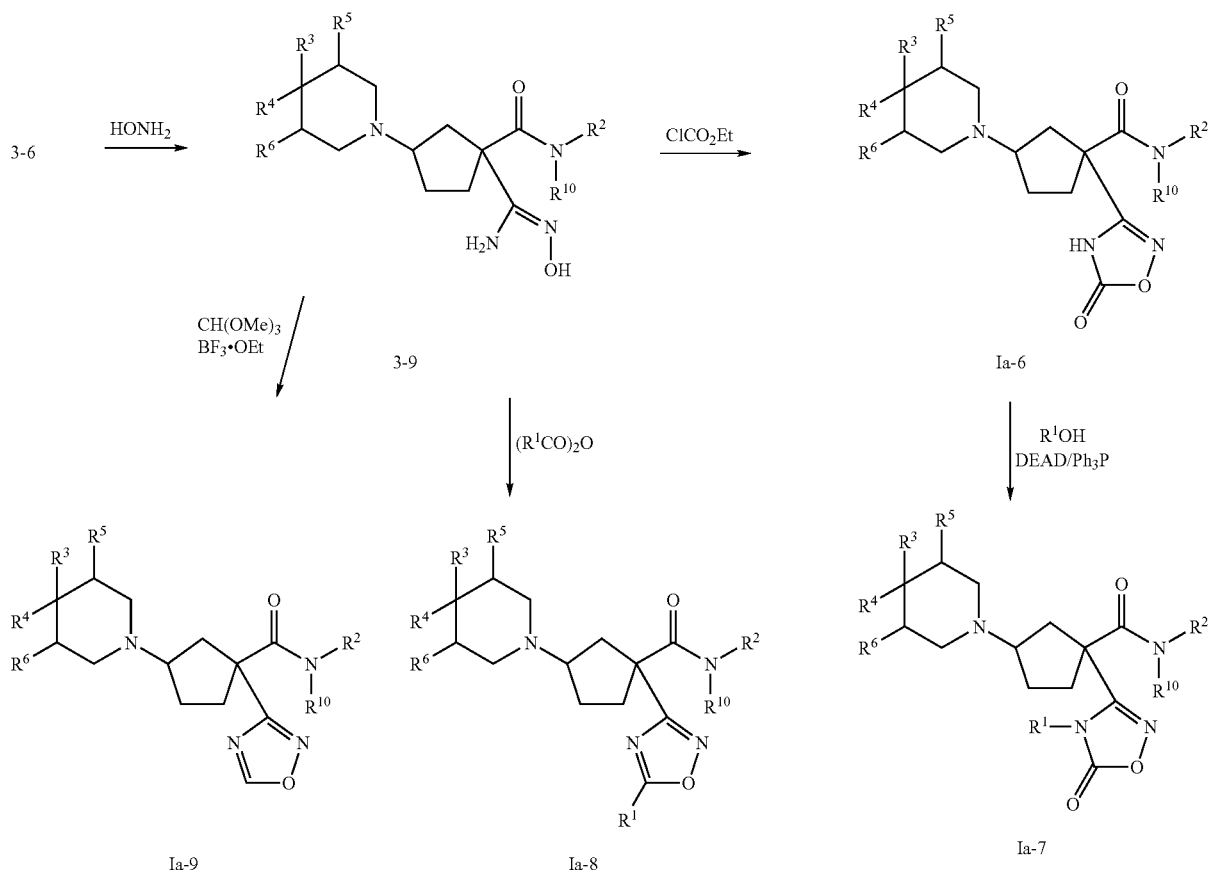

The intermediate 3-6 can also be converted into the intermediate 3-9 by treatment with hydroxylamine. Various heterocycles Ia-6, Ia-7, Ia-8, Ia-9, etc, could then be prepared by standard heterocycle formation conditions as depicted in the Scheme 3C.

For the preparation of the amino substituted heterocycles such as aminothiazole type of compounds, the procedure depicted in the Scheme 1 needs to be modified due to prerequisite protection of amino group during di-alkylated formation of cyclopentene intermediate (Scheme 4). Free aminothiazole acetate 4-1 can be converted into benzophenone Schiff base 4-2 by heating neat mixture of the ester and benzophenone imine. The cyclization of the Schiff base 4-2 with cis-1,4-dichloro-2-butene 1-2 gives the ester 4-3 using a strong base such as sodium hydride, sodium, lithium or potassium hexamethyl-disilazide, lithium diisopropylamide, and the like in an appropriate solvent such as DMF, DMPU, DME or a mixture of them (Depres, J.-P.; Greene, A. E. J. Org. Chem. 1984, 49, 928-931). Hydrolysis of the Schiff base is performed under standard acidic condition to give the intermediate 4-4 which is further converted into the bis-Boc-protected intermediate ester 4-5. Hydroboration of olefin 4-5,

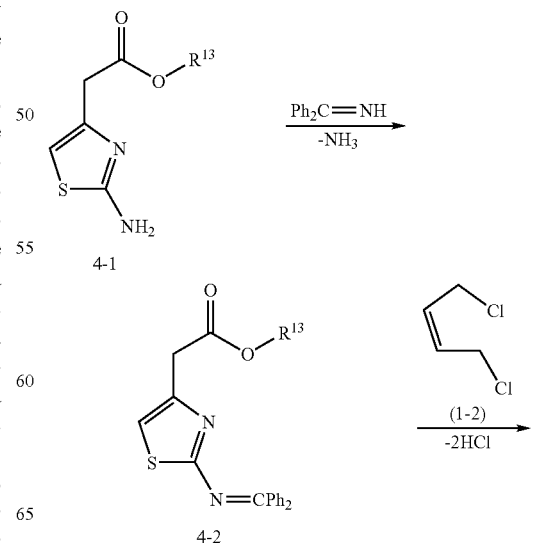

-continued

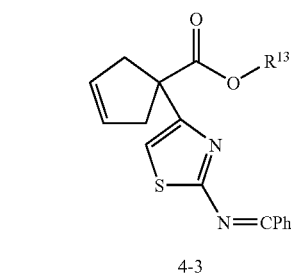
4-3

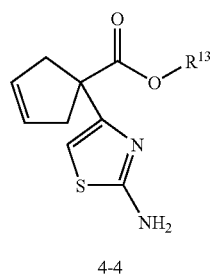
4-4

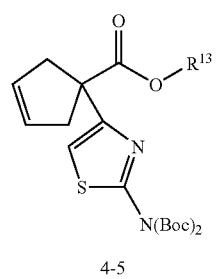
4-5

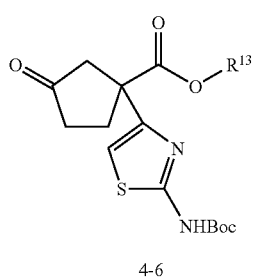
4-6

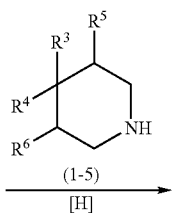
(1-5)
[H]

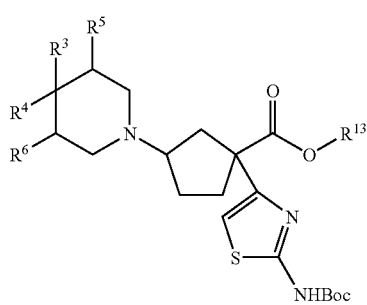
4-7

-continued

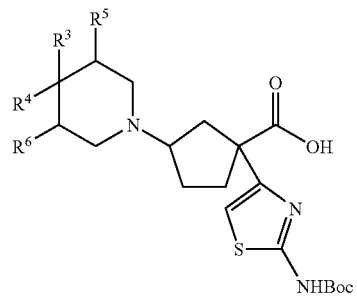
4-8

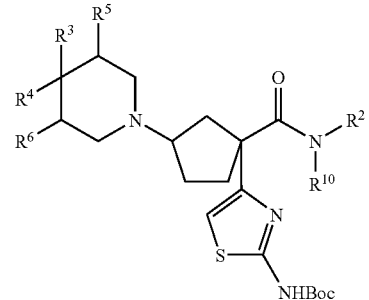
4-9

The intermediate esters 4-7, formed in the above mentioned transformations represent in general a mixture of 1,3-cis- and 1,3-trans-diastereoisomers. A diastereoisomeric separation could be accomplished later, after the esters 4-7 were hydrolytically cleaved to yield the respective acids 4-8. This selective hydrolysis was readily accomplished under usual conditions, including lithium, sodium or potassium hydroxide at ambient to elevated temperatures. These diastereoisomers could be separated by flash chromatography or crystallization from a variety of solvents taking advantage of the finding, that the cis-diastereoisomeric acids are less soluble, when compared to their trans-epimers. The compounds of formula 4-9 are then formed from the acids 4-8 and amines 1-8 under standard amide-bond forming reaction conditions, including carbodiimide reagents, such as DCC, EDC and catalysts such as DMAP, HOAT or HOBT.

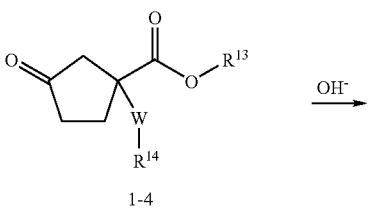
1-4

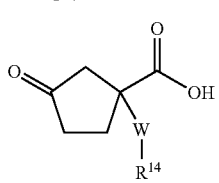
1-10

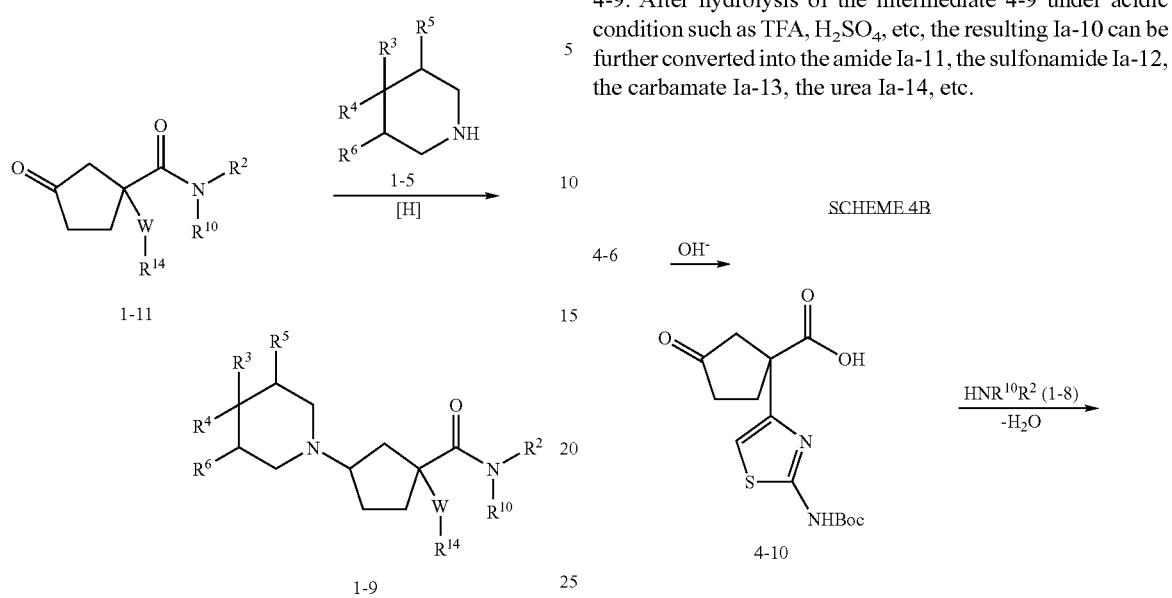
As depicted in the Scheme 4A, a variety of the compounds of the formula Ia can be prepared based on the intermediate 4-9. After hydrolysis of the intermediate 4-9 under acidic condition such as TFA, $H_2SO_4$, etc, the resulting Ia-10 can be further converted into the amide Ia-11, the sulfonamide Ia-12, the carbamate Ia-13, the urea Ia-14, etc.
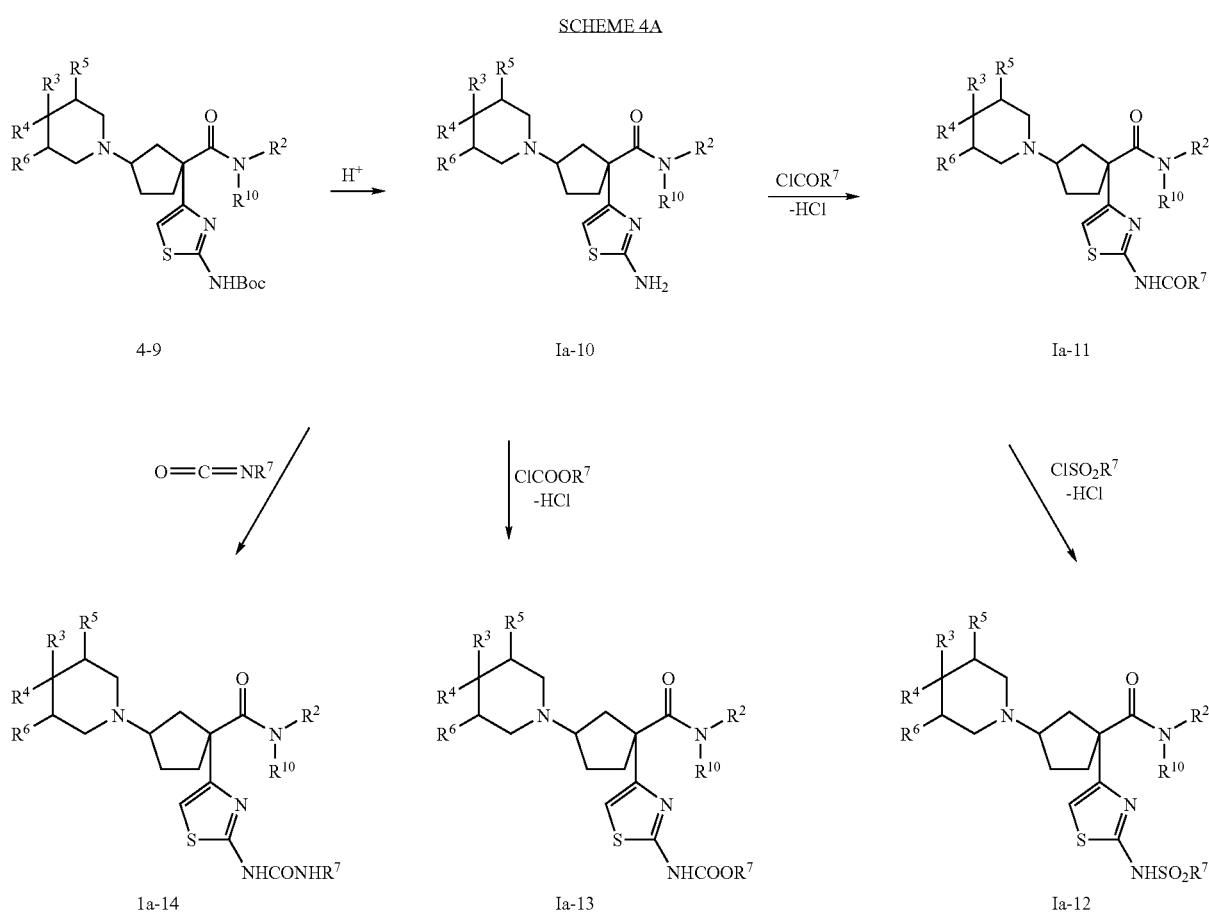

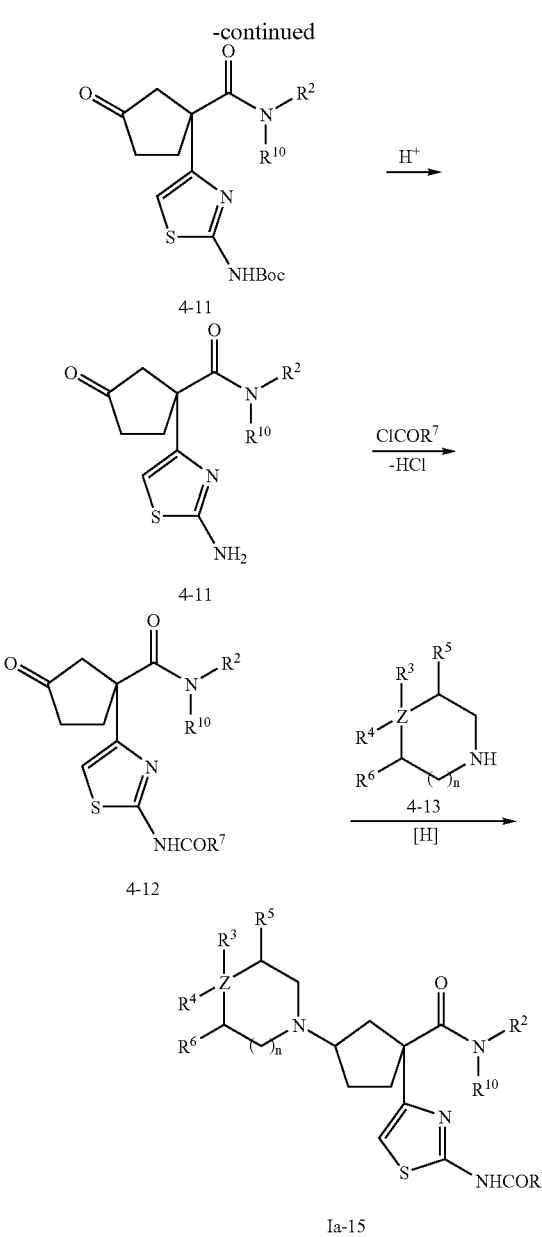

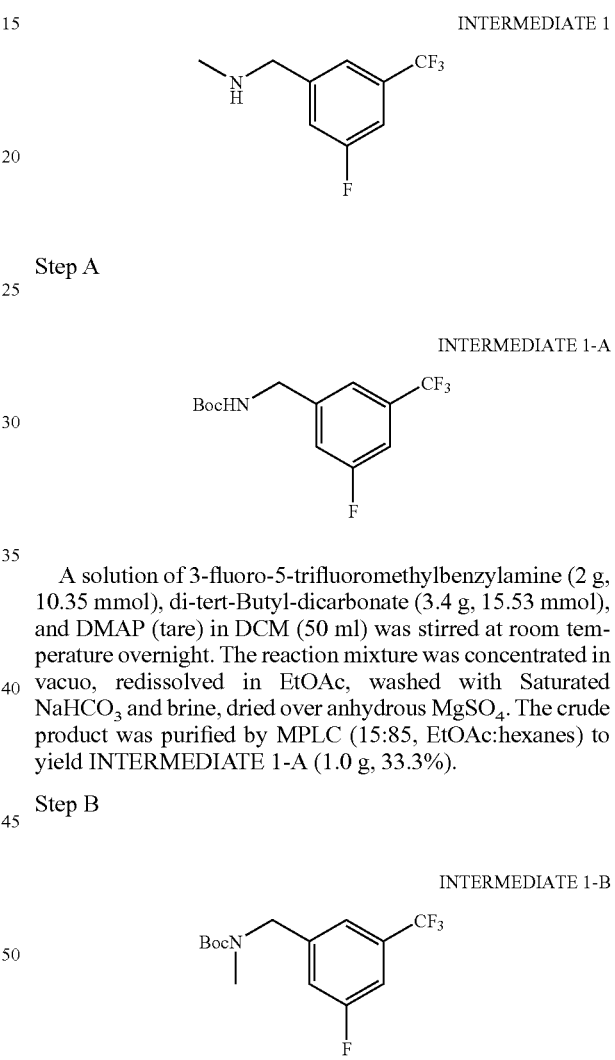

A second route has also been developed to introduce a variety of amines into the final product using the procedure depicted in the Scheme 4B. The keto ester 4-6 is hydrolyzed into the keto acid 4-10 under standard conditions such as lithium, sodium and potassium hydroxide. The following coupling with the amine 1-8 gives the keto amide 4-11 which can ben converted into the aminothiazole 4-11 and 4-12. The reductive amination of the ketone 4-12 with a variety of amines 4-13 provides the compounds of the formula Ia-15 as a mixture of 1,3-cis and 1,3-trans isomers which can be further separated into cis or trans isomer on preparative MPLC, TLC or HPLC.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried, out on silica gel (230-400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

INTERMEDIATE 1

Step A

INTERMEDIATE 1-A

A solution of 3-fluoro-5-trifluoromethylbenzylamine (2 g, 10.35 mmol), di-tert-Butyl-dicarbonate (3.4 g, 15.53 mmol), and DMAP (tare) in DCM (50 ml) was stirred at room temperature overnight. The reaction mixture was concentrated in vacuo, redissolved in EtOAc, washed with Saturated $NaHCO_3$ and brine, dried over anhydrous $MgSO_4$. The crude product was purified by MPLC (15:85, EtOAc:hexanes) to yield INTERMEDIATE 1-A (1.0 g, 33.3%).

Step B

INTERMEDIATE 1-B

60% NaH (205 mg, 5.12 mmol) was suspended in DMF (25 mL) under nitrogen. The mixture was cooled to −78° C. before INTERMEDIATE 1-A (1.0 g, 3.41 mmol) and MeI (640 μL, 10.2 mmol) were added. The solution was stirred at −78° C. for another 30 minutes before raised to room temperature. The reaction was diluted with ether, washed with water (3×), dried over anhydrous $MgSO_4$, and concentrated in vacuo. The crude product was purified by MPLC (10:90, EtOAc:hexanes) to yield 5-C (823 mg, 78.5%). 1H NMR (500 MHz, CDCl3) δ 7.30 (s, 1H), 7.25 (d, J=8.0 Hz, 1H), 7.14 (d, J=8 Hz, 1H), 4.47 (s, 2H), 2.88 (d, J=14.5 Hz, 3H), 1.49 (d, J=10.3 Hz, 9H).

Step C

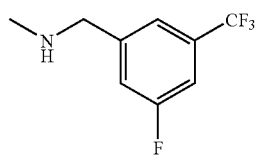

INTERMEDIATE 1-B (823 mg, 2.68 mmol) was dissolved in 4N HCl in dioxane (10 ml). Upon on completion of reaction, the solution was concentrated down to yield Intermediate 5 (614 mg, 94.3%). 1H NMR (400 MHz, CD3OD) δ 7.72 (s, 1H), 7.60 (t, J=4.5 Hz, 2H), 4.31 (s, 2H), 2.76 (s, 3H).

INTERMEDIATE 2

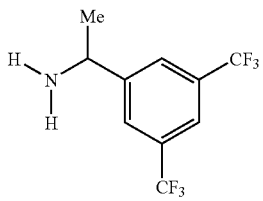

Step A:

INTERMEDIATE 2-A

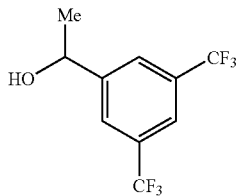

To a solution of bis(trifluoromethyl)benzaldehyde (20 g, 0.0826 mol) in 200 mL of THF at −78 C was added dropwise a solution of 84 mL of methylmagnesium bromide (1M, 0.084 mol) in butyl ether. The temperature was raised up to RT. The entire mixture was poured into a stirred mixture of ammonium chloride, ice and water (1000 mL), extracted with ethyl acetate (2×1000 mL). The organic phases were dried over NaSO4. Evaporation in vacuo afforded the title compound as a light yellow liquid (20.64 g, 98%), which was used directly for further conversion.

Step B:

INTERMEDIATE 2-B

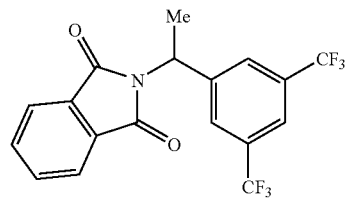

To a stirred solution of INTERMEDIATE 2-A (20.64 g, 0.08 mol), phthalimide (11.76 g, 0.08 mol) and triph-enylphosphine (22.6 g, 0.1 mol) in 150 mL of THF at 0 C was added dropwise a solution of DEAD (17.4 g, 0.1 mol) in 100 mL of THF in 30 min. The mixture was then stirred at RT overnight, condensed in vacuo. Flash chromatography on silica gel (500 g) afforded the title compound as a light yellow solid. ¹H NMR (400 MHz, CD3Cl): δ 1.96 (d, 3H), 5.64 (q, 1H), 7.70 (m, 2H), 7.79 (s, 1H), 7.80 (m,2H), 7.96 (s, 2H).

Step C:

INTERMEDIATE 2-C

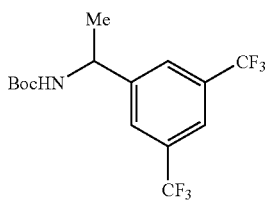

A mixture of INTERMEDIATE 2-B (all material, ~0.076 mol) and hydrazine (3.2 g, 0.1 mol) in 500 mL of ethanol was stirred at 80° C. for 2 h. The flask was put into refrigerator overnight. The solid was removed by filtration and washing with ethanol. The filtrates were combined and evaporated in vacuo. The above residue was stirred with di-tert-butyl dicarbonate (17 g, 0.08 mol) in 200 mL of dioxane for 30 min, evaporated in vacuo. The residue was purified by flash chromatography on silica gel (400 g) using 30% EtOAc/hexanes. The title compound (20.7 g) was obtained as a white solid. ¹H NMR (400 MHz, CD3OD): δ 1.40 (s, 9H), 1.71 (d, 3H), 4.50 (m, 1H), 7.75 (s,3H).

Step E:

INTERMEDIATE 2

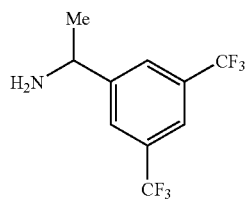

INTERMEDIATE 2-C (20.7 g) was stirred with a solution of 100 mL of 4M HCl dioxane for 2 h. The mixture was evaporated and dried in vacuo afford the title compound as a white solid (15.6 g). ¹H NMR (400 MHz, CD3OD): δ 1.69 (d, 2H), 4.75 (q, 1H), 8.05 (s, 1H), 8.16 (s,2H).

INTERMEDIATE 3

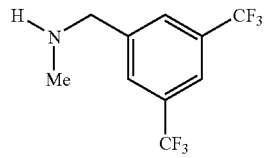

Step A:

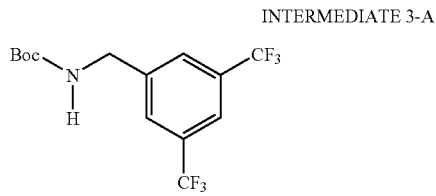

INTERMEDIATE 3-A

A mixture of 1,3-bis-trifluoromethylbenzylamine hydrochloride (10 g, 36 mmol), di-tert-butyl dicarbonate (8.73 g, 40 mmoL) and TEA (5.6 mL, 40 mmol) in 50 mL of DCM was stirred overnight, washed with 2N aq. HCl, sat. aq. NaHCO3 and water, dried over Na2SO4 and evaporated, dried in vacuum. The title compound (12.7 g) was obtained as a white solid. $^1$H NMR (400 MHz, CD3OD): δ 1.51 (s, 9H), 4.40 (s, 2H), 5.28 (broad, 1H), 7.73 (s,2H), 7.76 (s, 1H).

Step B:

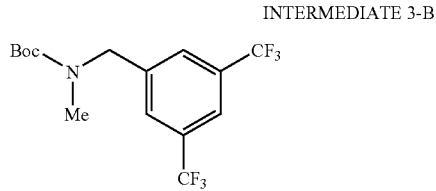

INTERMEDIATE 3-B

NaH (60% oil, 1.6 g) was added to a stirred solution of INTERMEDIATE 3-B (12.7 g, 37 mmol) in 200 mL of DMF at 0° C. in multiple portions. The resulting mixture was stirred for another 1 h, added neat iodomethane (5.7 g, 40 mmol). The mixture was stirred at RT for additional 2 h, dumped into a mixture of ice-water, extracted with ether repeatedly. The combined extracts were washed with water, dried over Na2SO4, evaporated, dried in vacuum. The title compound (11.5 g) was obtained as a yellow oil. $^1$H NMR (400 MHz, CD3OD): δ 1.45 (s, 9H), 2.89 (s, 3H), 4.51 (s, 2H), 7.67 (s,2H), 7.77 (s, 1M).

Step C:

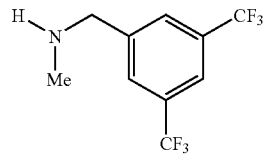

A mixture of INTERMEDIATE 3-B (11.5 g) with 100 mL of 4N HCl in dioxane was stirred at RT for 1 h, added 200 mL of hexane. The resulting precipitate was collected by filtration and washed with hexane, dried in vacuum. The title compound (7.0 g) was obtained as a white solid. $^1$H NMR (400 MHz, CD3OD): δ 2.78 (s, 3H), 4.40 (s, 2H), 8.10 (s, 1H), 8.19 (s,2H).

EXAMPLE 1

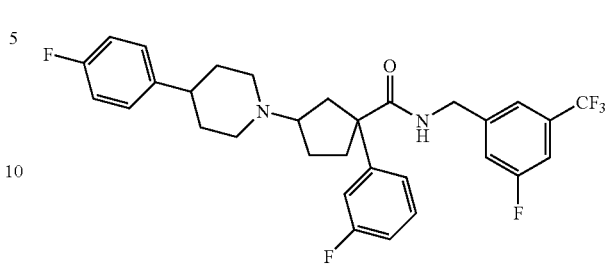

1-(3-fluorophenyl)-3-[4-(4-fluorophenyl)piperidin-1-yl]-N-[3-fluoro-5-(trifluoromethyl)benzyl]cyclopentanecarboxamide Step A

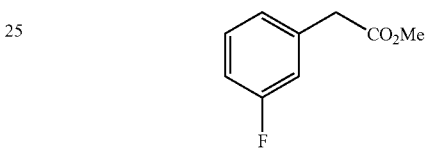

Thionyl chloride (9.5 mL, 130 mmol) was added dropwise to methanol (225 mL) before 3-fluorophenyl acetic acid (20 g, 130 mmol) was dumped into the solution. The reaction mixture was refluxed for 1 hour before concentrated in vacuo to yield the title compound (23.4 g, 107%). 1H NMR (400 M CDCl3) δ 7.30 (m, 1H), 7.02 (m, 3H), 3.73 (s, 3H), 3.64 (s, 2H).

Step B

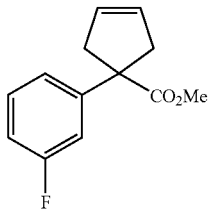

The ester (23.25 g, 138 mmol, from Step A) and 1,4-dichloro-cis-butene (15 mL, 0.14 mol) were dissolved in DME (200 mL) at 0° C. under nitrogen before 60% NaH (14 g, 350 mmol) was added. The reaction mixture was stirred for 12 hours before dumped in ice water and extracted with ether (3×). Combined ether layers was washed with water and saturate NaCl solution, dried over anhydrous MgSO$_4$, and concentrated in vacuo. The crude product was purified by vacuum distillation (0.11 mm, 92-101° C.) to yield the title compound (20 g, 60.2%), which contained about 20% of three membered ring side product. 1H NMR (500 MHz, CDCl3) δ 7.29 (m, 1H), 7.10 (m, 2H), 6.97 (m, 1H), 5.78 (s, 2H), 3.68 (s, 3H), 3.41 (d, J=15.1 Hz, 2H), 2.78 (d, J=14.6 Hz, 2H).

Step C

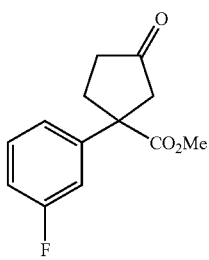

The cyclopentene (12.5 g, 56.8 mmol, from Step B), 1M BH$_3$ (28.4 mL, 28.4 mmol), and THF (100 mL) were mixed together and stirred at room temperature under nitrogen. Upon the disappearance of the starting material, the reaction mixture was concentrated to dryness in vacuo and redissolved in DCM. Anhydrous MgSO$_4$ (75 g) and PCC (49 g, 227.2 mmol) were added. The reaction mixture was stirred for 24 hours before filtered through silica gel. The precipitate was suspended in DCM and ethyl acetate. The solution was refluxed for 20 minutes before hot filtered through silica gel to recover as much product as possible. The combined filtrate was concentrated in vacuo and purified by flash column chromatography (30:70; ethyl acetate:hexanes) to yield the title compound (6.46 g, 48.2%). 1H NMR (400 MHz, CDCl3) δ 7.35 (m, 1H), 7.14-7.00 (m, 4H), 3.69 (s, 3H), 3.25 (dd, J=17.9 Hz, 2.1 Hz, 1H), 2.98 (m, 1H), 2.61 (d, J=17.9 Hz, 1H), 2.41-2.28 (m, 3H).

Step D

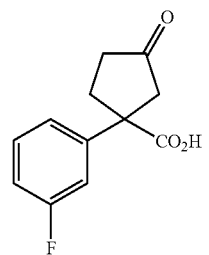

LiOH (2.05 g, 25.4 mmol) was dissolved first in water (5 mL) before a solution of the ketone (3 g, 12.7 mmol, from Step C) in methanol (25 mL) was added. The reaction mixture was stirred at room temperature for 5 hours before concentrated in vacuo. The concentrate was redissolved in water and washed with ether. The aqueous layer was acidified to pH2-3 by 2N HCl solution and extracted with ether (4×). Combined organic layer was dried over anhydrous MgSO$_4$, filtered, and concentrated in vacuo to yield the title compound (2.678 g, 94.9%). The crude product was used on the next step.

Step E

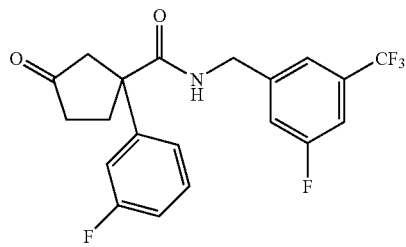

The keto acid (1.34 g, 6.57 mmol, from Step D), 3-fluoro-5-trifluoromethyl benzylamine (972 µL, 6.57 mmol), HOAT (895 mg, 6.57 mmol), EDC (1.9 g, 9.85 mmol) were mixed together in DCM and stirred for 16 hours under room temperature before washed with 1N HCl solution, saturated NaHCO$_3$ solution, water, and saturated NaCl solution, dried over anhydrous MgSO$_4$, and concentrated in vacuo. The crude product was purified by MPLC (50:50, ethyl acetate:hexanes) to yield pure the title compound (1.156 g, 44.3%). 1H NMR (400 MHz, CDCl3) δ 7.44 (m, 1H), 7.21 (d, J=8.0 Hz, 1H), 7.17 (m, 4H), 6.99 (d, J=9.0 Hz, 1H), 5.64 (s, 1H), 4.41 (t, J=5.9 Hz, 2H), 3.21 (d, J=17.6 Hz, 1H), 2.80 (m, 1H), 2.64-2.44 (m, 3H), 2.35 (m, 1H).

Step F

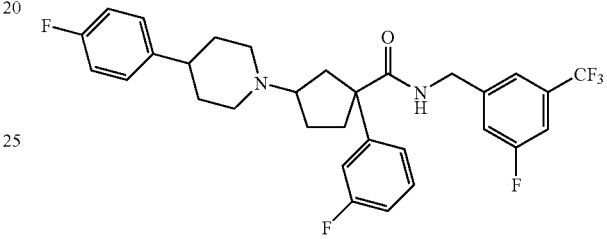

The keto amide (100 mg, 0.252 mmol, from step E), 4-fluoro-4-phenyl piperidine (55 mg, 0.252 mmol), DIEA (66 µL, 0.378 mmol), NaBH(OAc)$_3$ (267 mg, 1.26 mmol), and molecular sieves were mixed together in DCM and stirred at room temperature for 24 hours. The reaction was concentrated and purified by preparative TLC (2.5:0.25:97.25, methanol:NH$_4$OH:DCM) to yield the final product of the title compound (93 mg, 66.0%). LC-MS for C$_{31}$H$_{30}$F$_6$N$_2$O[M$^+$H]$^+$ calculated 561.23, found 561.25.

EXAMPLE 2

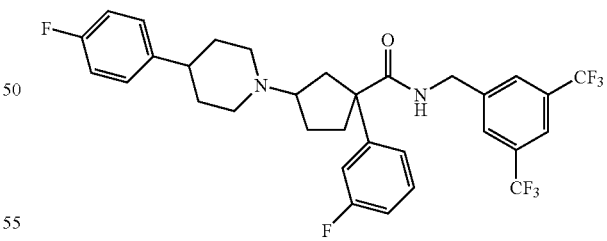

Example 2 was synthesized from the keto acid (Example 1, Step D) and bis-trifluoromethylbenzylamine hydrochloride using the same procedure as detailed in EXAMPLE 1. LC-MS for C$_{32}$H$_{30}$F$_8$N$_2$O [M$^+$H]$^+$ calculated 611.22, found 611.2.

A variety of other aromatic substitutions on the W—R$^1$ position of cyclopentane ring was prepared using the reaction scheme illustrated in Example 1. The table below summarizes these compounds.

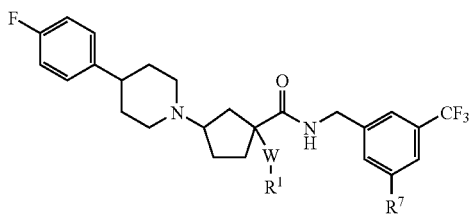

| Ex. | W-R¹ | R⁷ | Molecular Formula | Calculated M⁺H⁺ | Found M⁺H⁺ |
|---|---|---|---|---|---|
| 3 | 3-MeOPh | F | C32H33F5N2O2 | 573.25 | 573.25 |
| 4 | 3-MeOPh | CF₃ | C33H33F7N2O2 | 623.24 | 623.25 |
| 5 | 2-Thienyl | F | C29H29F5N2OS | 549.15 | 549.25 |
| 6 | 2-Thienyl | CF₃ | C30H29F7N2OS | 599.19 | 599.35 |
| 7 | 3-Thienyl | F | C29H29F5N2OS | 549.15 | 549.25 |
| 8 | 3-Thienyl | CF₃ | C30H29F7N2OS | 599.19 | 599.35 |
| 9 | Phenyl | F | C31H31F5N2O | 543.24 | 543.25 |
| 10 | Phenyl | CF₃ | C32H31FN2O | 593.23 | 593.20 |

INTERMEDIATE 4

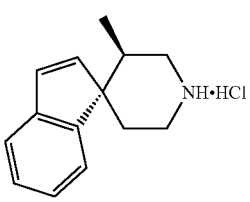

Step A:

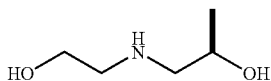

To a cooled (0° C.) solution of ethanolamine (41.8 g, 0.685 mol) in water (90 mL) was added neat (R)-propylene oxide (4.97 g, 85.6 mmol), dropwise. After 1 h at 0° C. the reaction was allowed to rise to rt and stirred overnight. The reaction mixture was concentrated at ~80° C. in vacuo to remove the water and most of the ethanolamine, to give 11.79 g of crude product, containing some residual ethanolamine. This material was used without further purification in Step B.

Step B:

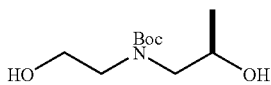

The diol prepared in Step A (11.8 g crude [~86% pure], ca. 83 mmol) was dissolved in DCM (150 mL) and treated with Boc₂O (23.4 g, 107 mmol) in DCM (75 mL) over 15 min. The reaction mixture was stirred over the weekend, concentrated, and purified by MPLC, eluting with 5% MeOH/EtOAc to provide 14.8 g (81%) of product.

Step C:

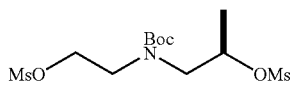

To a solution of the Boc-protected diol prepared in Step B (13.2 g, 60.3 mmol) and triethylamine (21.0 mL, 15.3 g, 151 mmol) in DCM (150 mL) at 0° C. was added dropwise methanesulfonyl chloride (9.56 mL, 14.1 g, 125 mmol). The reaction mixture was then stirred for 1.5 h, diluted with more DCM (100 mL) and washed with 3N HCl (250 mL). The aqueous layer was extracted again with DCM (200 mL), and the organic layers were combined and washed with 1N HCl (250 mL), saturated NaHCO₃ solution (250 mL), and brine (250 mL). The organic layer was dried over MgSO₄, filtered, and concentrated to give 22.8 g of crude bis-mesylate, which was used immediately. If not used immediately the bis-mesylate underwent decomposition.

Step D:

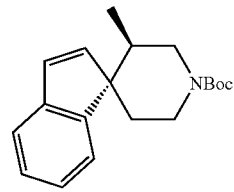

Indene (7.03 mL, 7.00 g, 60.3 mmol) was added dropwise over 4 min to a 1.0 M THF solution of LHMDS (127 mL, 127 mmol) at 0° C. After stirring for an additional 30 min., this solution was transferred via cannula to a solution of bis-mesylate (22.6 g, 60.3 mmol), prepared as described in Step C above, in THF (75 mL) at 0° C. The mixture was stirred for 2 h, warmed to rt and stirred overnight. The reaction mixture was partially concentrated and then partitioned between ethyl acetate and water. The organic layer was extracted again with ethyl acetate and the organic layers were combined. The organic phase was then washed with brine, dried over MgSO₄, filtered and concentrated to give 17.3 g of crude product. Purification by MPLC, eluting with 15% ethyl acetate/hexane, afforded 9.51 g (53%) of piperidine as a ~3:1 mixture of trans to cis (determined by H NMR). The mixture was crystallized from hot hexane to give 6 g (33%) of pure trans isomer (>20:1 by H NMR).

H NMR (CDCl₃, 400 MHz): δ 7.29 (dt, J=6.4, 1.6 Hz, 1H), 7.20 (m, 3H), 6.83 (d, J=6.0 Hz, 1H), 6.67 (d, J=5.6 Hz, 1H), 4.20 (br s, 2H), 2.97 (br t, J=3.2 Hz, 1H), 2.69 (br t, J=2.4 Hz, 1H), 2.16 (m, 1H), 2.07 (dt, J=4.4, 13.2 Hz, 1H), 1.49 (s, 9H), 1.25 (m, 1H), 0.31 (d, J=6.8 Hz, 3H).

Step E:

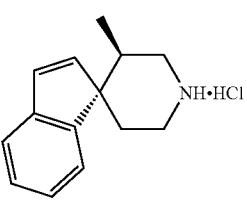

The Boc-piperidine prepared in Step D (4.35 g, 14.5 mmol) was dissolved in an anhydrous 4 N HCl solution in dioxane and stirred at rt for 1 h. The reaction mixture was then concentrated to afford 3.81 g of product.

EI-MS calc. for C14H17N: 199. Found: 200 (M)+.

EXAMPLE 11

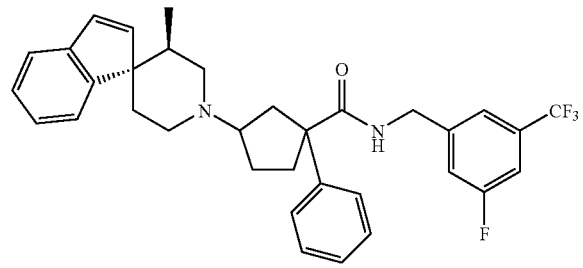

Step A:

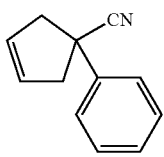

To a solution of benzyl cyanide (47 g, 0.40 mol) in 93:7 DME/HMPA (800 mL) was added solid LiH (7.95 g, 1.00 mol) under a steady flow of nitrogen. Then cis-1,4-dichlorobutene (47.2 mL, 0.450 mol) was added in one portion and the mixture was stirred at 60° C. overnight. The reaction mixture was quenched with ice, then extracted with 20% ether/hexane. The organic extracts were dried over anhydrous MgSO4, filtered, and concentrated. The residue was purified by distillation (110-115° C., ~1 mm Hg), affording 49 g of a light yellow oil.

Step B:

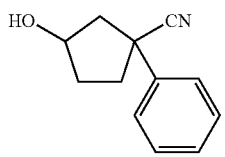

A solution of the alkene prepared as described in Step A above (10.6 g, 63.0 mmol) in THF (40 mL) at 0° C. was treated dropwise with 1.0 M BH3.THF in THF (41.6 mL, 41.6 mmol). The reaction mixture was warmed to room temperature and stirred for 2 h, at which point some starting material remained. An additional amount of 1.0 M BH3.THF in THF (20.8 mL, 20.8 mmol) was added, and after 1 h, the reaction mixture was cooled to 0° C. and quenched with 10 mL of water (slowly at first). Then 3 N NaOH (30 mL) was added, followed by ethanol (50 mL) and 30% hydrogen peroxide solution (50 mL). The reaction mixture was stirred at room temperature overnight. Then Na2SO3 (5.96 g) was added and the reaction mixture was stirred for one h. The reaction mixture was extracted three times with ethyl acetate and the combined organic layers were washed with brine, dried over anhydrous MgSO4, filtered, and concentrated. Purification by MPLC (silica, 70% ethyl acetate/hexane) gave 4.39 g of a yellow oil.

ESI-MS calc. for C12H13NO: 187. Found: 188 (M+H).

Step C:

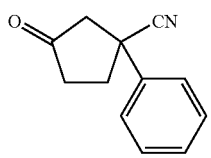

A solution of oxalyl chloride (87 μL, 1.00 mmol) in DCM at −78° C. was treated dropwise with a solution of DMSO (142 μL, 2.00 mmol) in DCM (total volume 1 mL). Then the alcohol prepared as described in Step B above (125 mg, 0.668 mmol) in DCM (2 mL) was added dropwise. Next, triethylamine (558 μL, 4.00 mmol) was added and the reaction mixture was allowed to warm to room temperature and stir for 30 min. The reaction mixture was then diluted with DCM and washed with water, then 1 N HCl solution, saturated NaHCO3 solution, and brine. The organic layer was dried over anhydrous MgSO4, filtered, and concentrated to afford 122 mg of crude product which did not require further purification.

Step D:

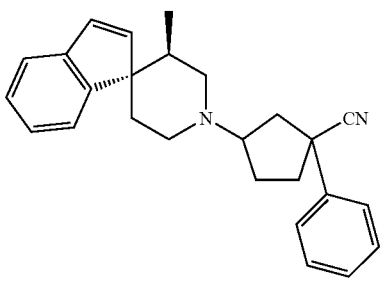

The cyclopentanone from Step D immediately above (115 mg, 0.621 mmol) was combined in DCM (3 mL) with 3-methylspiroindenepiperidine Intermediate 1 (161 mg, 0.684 mmol), triethylamine (95 μL, 0.68 mmol), and sodium tiacetoxyborohydride (263 mg, 1.24 mmol). The resulting mixture was stirred at room temperature for 24 h. The reaction mixture was then filtered through a celite plug, washing with ethyl acetate. The filtrate was washed with saturated NaHCO3 solution, then with brine, dried over anhydrous MgSO4, filtered, and concentrated. Purification by preparative TLC (silica, 0.1/0.9/99 of NH4OH/methanol/DCM) gave 100 mg of the product aminonitrile.

ESI-MS calc. for C26H28N2: 368. Found: 369 (M+H).

Step E:

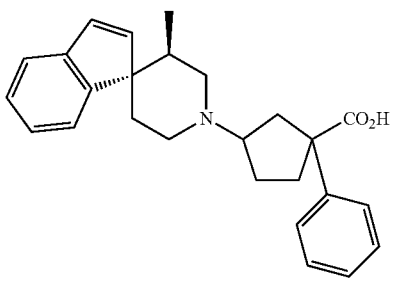

A solution of the aminonitrile prepared as described in Step D above (100 mg, 0.272 mmol) in water/ethanol (1:1, 4 mL)

was treated with sodium hydroxide (459 mg, 11.5 mmol) and the reaction mixture was subsequently stirred at reflux overnight. Then 1 N HCl in ether was added dropwise until the pH was neutral to pH paper. The mixture was then extracted with CHCl$_3$ three times. The combined organic layers were washed with brine, dried over anhydrous MgSO$_4$, filtered, and concentrated. Only a single isomer (cis) was obtained (48 mg) with the trans-isomer presumably lost during workup due to higher water solubility.

ESI-MS calc. for C26H29NO2: 387. Found: 388 (M+H).

Step F:

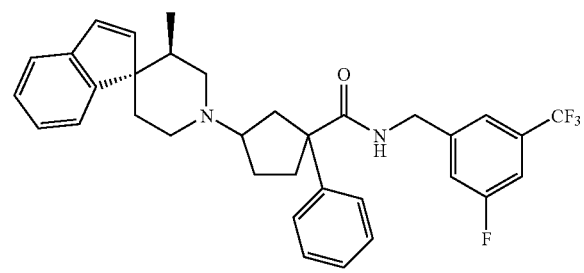

The aminoacid prepared as described in Step E above (48 mg, 0.12 mmol) was combined with 3-fluoro-5-trifluoromethylbenzylamine (36 μL, 0.25 mmol), EDC (47 mg, 0.25 mmol) and DMAP (~3 mg) in DCM (3 mL). The reaction mixture was stirred at room temperature for 3 days. The reaction mixture was then diluted with DCM and washed with water, then brine. The organic layer was dried over anhydrous MgSO$_4$, filtered, and concentrated. Purification by preparative TLC (silica, 0.2/1.8/98 of NH$_4$OH/methanol/DCM) gave 41 mg of a yellow solid, existing as a racemic mixture of cis-isomers.

ESI-MS calc. for C34H34F4N2O: 562. Found: 563 (M+H).

The racemic mixture of cis-isomers prepared as described in Example 11, Step F could be resolved into two pure single isomers by chiral HPLC (ChiralPak OD column).

The following Table shows related compounds which were prepared in the same fashion as described in Example 11, or with minor modifications.

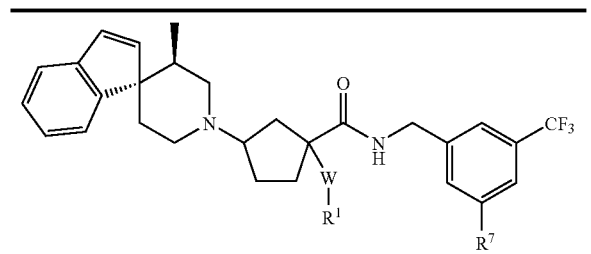

| Ex. | W-R$^1$ | R$^7$ | Calc. MW | ESI-MS found (M + H)$^+$ |
|---|---|---|---|---|
| 12 | Ph | CF$_3$ | 612 | 613 |
| 13 | m-Br-Ph | F | 641 | 643 |
| 14 | m-Br-Ph | CF$_3$ | 691 | 693 |
| 15 | m-F-Ph | F | 580 | 581 |
| 16 | m-F-Ph | CF$_3$ | 630 | 631 |
| 17 | p-F-Ph | F | 580 | 581 |
| 18 | p-F-Ph | CF$_3$ | 630 | 631 |

Another series of compounds were synthesized with phenyl piperidine instead of 4-fluoro phenyl piperidine. They were made according to procedures detailed in Example 1 with exception that Step F proceeded before Step E. Cis and trans acids in Step F were resolved (see Scheme 1). The table below summarizes these compounds.

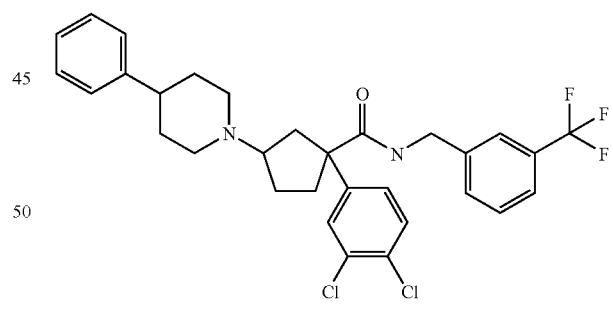

| Ex. | R$^7$ | R$^{10}$ | 1,3-Relationship | Molecular Formula | Calc. M$^+$H$^+$ | Found M$^+$H$^+$ |
|---|---|---|---|---|---|---|
| 19 | CF$_3$ | H | Cis | C32H32F6N2O | 575.24 | 575.25 |
| 20 | CF$_3$ | H | Trans | C32H32F6N2O | 575.24 | 575.35 |
| 21 | F | H | Cis | C31H32F4N2O | 525.25 | 525.25 |
| 22 | F | H | Trans | C31H32F4N2O | 525.25 | 525.25 |
| 23 | F | Me | Cis | C32H34F4N2O | 539.26 | 539.30 |

EXAMPLE 24

A mixture of the amino acid (50 mg, 0.12 mmol, see Scheme 1), 3-CF3 benzylamine (17 uL, 0.12 mmol), HOAT (16 mg, 0.12 mmol), EDC (35 mg, 0.18 mmol), and DCM (2 mL) was stirred at room temperature overnight. The crude mixture was purified on a preparation plate (3/97 mehtanol/DCM) to yield Example 24 (60 mg, 82.2%). LC-MS for C$_{31}$H$_{31}$N$_2$OCl$_2$F$_3$ [M$^+$H]$^+$ calculated 575.18, found 575.2.

A number of compounds were synthesized using the procedure detailed in Example 24 with different benzylamines. These compounds are summarized in the table below.

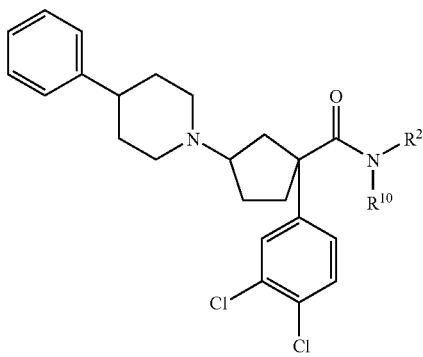

| Ex. | HNR²R¹⁰ | Molecular Formula | Calc. M⁺H⁺ | Found M⁺H⁺ |
|---|---|---|---|---|
| 25 | 2-CF₃-benzyl-NH₂ | C31H31N2OCl2F3 | 575.18 | 575.20 |
| 26 | 4-CF₃-benzyl-NH₂ | C31H31N2OCl2F3 | 575.18 | 575.20 |
| 27 | 3,5-diCl-benzyl-NH₂ | C30H30N2OCl4 | 575.11 | 577.15 |
| 28 | 3,4-diCl-benzyl-NH₂ | C30H30N2OCl4 | 575.11 | 577.15 |
| 29 | 3,5-bis(CF₃)-α-methylbenzyl-NH₂ | C33H32N2OCl2F6 | 589.19 | 589.30 |
| 30 | 3-CF₃-α-methylbenzyl-NH₂ | C32H33N2OCl2F3 | 657.18 | 657.25 |

INTERMEDIATE 5

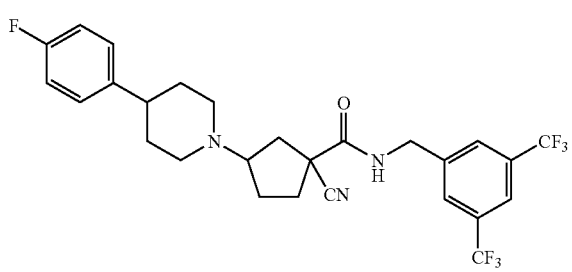

Step A:

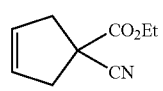

A solution of ethyl cyanoacetate (40.9 g, 0.361 mol) in 400 mL DMF was cooled to 0° C. and treated under a steady stream of N₂ with lithium hydride (7.18 g, 0.903 mol) in multiple portions. After hydrogen evolution subsided, cis-1, 4-dichloro-2-butene (51.9 g, 0.415 mol) was added dropwise by addition funnel. The reaction became very thick during the addition, requiring the addition of 200 mL of DMF to aid in stirring. The reaction mixture was permitted to warm to room temperature and was stirred for 1 h. The reaction mixture was then poured into a 1:1 mixture of water/ice, which was in turn extracted twice with ether. The ethereal layers were combined and washed five times with water, and once with brine. The ethereal phase was then dried over $MgSO_4$, filtered and concentrated. The resulting crude product was distilled using a short path distillation apparatus (1 mm Hg, bath temperature=100° C., head temperature=75° C.), giving 25.8 g of the desired product (43%).

1H NMR (CDCl$_3$, 500 MHz) δ 5.70 (s, 2H), 4.27 (q, J=7 Hz, 2H), 3.10 (m, 4H), 1.34 (t, J=7 Hz, 3H).

Step B:

A solution of the cyclopentene prepared in Step A above (17.5 g, 0.106 mol) in 100 mL of THF was cooled to −78° C. and treated with BH$_3$.THF (1 M solution in THF, 63.5 mL, 63.5 mmol) dropwise. The reaction mixture was stirred at −78° C. for 0.5 h, then warmed to room temperature and stirred for an additional 1 h. TLC indicated that the reaction was incomplete so the mixture was cooled back to −78° C. and treated with more BH$_3$.THF solution (1 M solution in THF, 42 mL, 42 mmol). The reaction mixture was then warmed to room temperature and stirred for 2 h. After storing overnight in a freezer, the reaction mixture was concentrated at room temperature and redissolved in DCM (500 mL). Then while stirring with an overhead mechanical stirring apparatus, premixed PCC (137 g, 0.635 mol) and magnesium sulfate (130 g) were added in portions over 15 minutes. The resulting exotherm was controlled with an ice bath. After stirring at room temperature for 3 h, the reaction mixture was filtered through a 3" plug of silica, washing the remaining solids three times with acetone. The filtrate was concentrated and filtered a second time through a 3" silica plug washing through with 50% ethyl acetate/hexane. The filtrate was concentrated and the residue was purified by flash chromatography (silica, 50% ethyl acetate/hexane) giving 4.63 g (24%) of product.

1H NMR (CDCl$_3$, 500 MHz) δ 4.35 (q, J=8.5 Hz, 2H), 2.94 (d, J=23 Hz, 1H), 2.78 (d, J=23 Hz, 1H), 2.51-2.70 (m, 4H), 1.38 (t, J=9 Hz, 3H).

Step C:

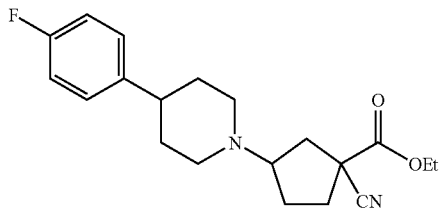

A solution of the ketone prepared as described in Step B above (3.57 g, 19.7 mmol) in DCM (75 mL) was treated with triethylamine (3.29 mL, 23.6 mmol), 4-(4-fluorophenyl)piperidine hydrochloride (5.10 g, 23.6 mmol), 4°A powdered molecular seives (5 g), and sodium triacetoxyborohydride (16.7 g, 78.8 mmol). The resulting mixture was stirred at room temperature for 72 h. The reaction mixture was then filtered through celite, washing with additional DCM. The filtrate was washed with saturated NaHCO$_3$ solution, water, and brine. The organic layer was dried over anhydrous MgSO$_4$, filtered, and concentrated. The crude product was purified by MPLC (silica, ethyl acetate, then 5% methanol/ethyl acetate, then 10% methanol/ethyl acetate) to give 4.45 g of product as a colorless oil (66%).

ESI-MS calc. for C20H25FN2O2: 344. Found: 345 (M+H).

Step D:

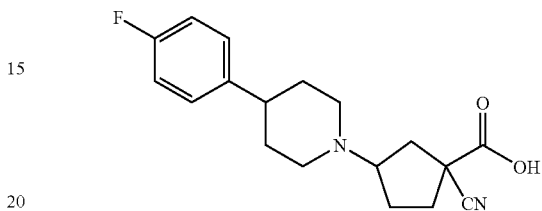

A solution of the aminoester prepared as described in Step C above (4.34 g, 12.6 mmol) in 1:1 THF/methanol (50 mL) was treated over a period of 5 min with a solution of LiOH.H$_2$O (2.64 g, 63.0 mmol) in water (25 mL). The reaction mixture was stirred at room temperature for 1 h, then neutralized with 3N HCl solution, and concentrated to remove the organic solvents. The aqueous mixture was diluted with brine and extracted three times with chloroform. The combined organic layers were dried over anhydrous MgSO$_4$, filtered, and concentrated. The crude product was purified by flash chromatography (silica, 10-20% methanol/DCM gradient), affording 1.64 g of the top spot corresponding to the cis-isomer (based on previous examples) and 1.27 g of the bottom spot corresponding to the trans-isomer (total yield: 73%). Top spot (cis-isomer): ESI-MS calc. for C18H21FN2O2: 316. Found: 317 (M+H). Bottom spot (trans-isomer): ESI-MS calc. for C18H21FN2O2: 316. Found: 317 (M+H).

Step E:

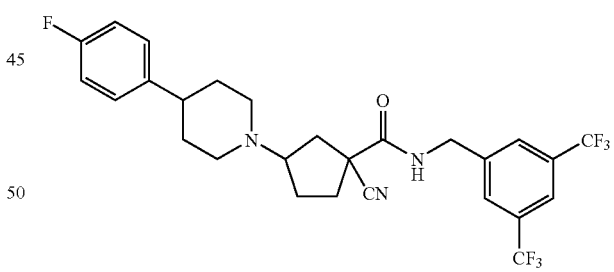

The cis-aminoacid prepared as described in the last step (1.40 g, 4.41 mmol) was combined with EDC (1.69 g, 8.82 mmol), 3,5-Bis(trifluoromethyl)benzylamine hydrochloride (1.85 g, 6.62 mmol), triethylamine (0.923 mL, 6.62 mmol), and DMAP (~100 mg) in DCM (50 mL). After stirring at room temperature for 2.5 h, the reaction mixture was diluted with DCM and washed with water twice, then brine. The organic layer was dried over anhydrous MgSO$_4$, filtered, and concentrated. The crude product was purified by MPLC (silica, 5% methanol/ethyl acetate) to afford 1.72 g of product (72%) with the amine and amide groups cis-to each other.

ESI-MS calc. for C27H26F7N3O: 541. Found: 542 (M+H).

INTERMEDIATE 6

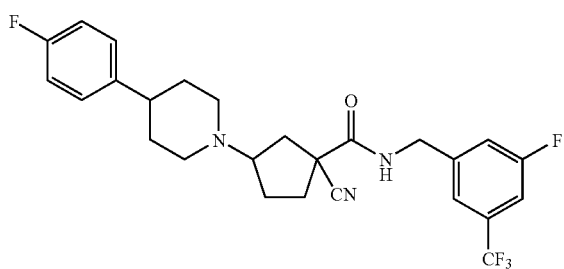

Intermediate 6 was prepared in the same fashion as intermediate 5, above, starting from the cis-aminoacid prepared as described in Step D (233 mg, 0.737 mmol) and giving after purification by preparative TLC (silica, 0.3/2.7/97 NH$_4$OH/MeOH/DCM) 286 mg of product (79%).

ESI-MS calc. for C27H26F5N3O: 491. Found: 492 (M+H).

INTERMEDIATE 7

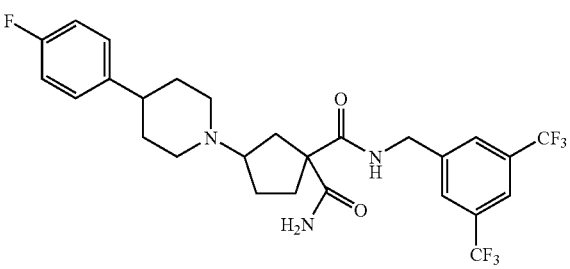

Intermediate 5 (50.4 mg, 0.0931 mmol) was dissolved in DMSO (1 mL) and treated with K$_2$CO$_3$ (3 mg), followed by 30% H$_2$O$_2$ solution (12 μL). The reaction mixture was stirred at room temperature for 0.5 h, then was quenched with 10% Na$_2$CO$_3$ solution. The aqueous mixture was extracted twice with ethyl acetate. The combined organic layers were washed four times with water and once with brine, then dried over anhydrous MgSO$_4$, filtered, and concentrated. The crude product (44.6 mg) was collected as a white solid and required no further purification.

ESI-MS calc. for C27H31F7N3O2: 559. Found: 560 (M+H).

INTERMEDIATE 8

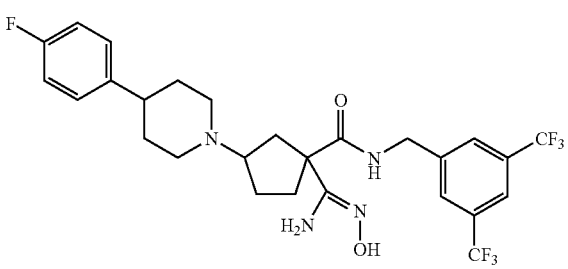

Triethylamine (248 μL, 1.78 mmol) was added to a suspension of hydroxylamine hydrochloride (124 mg, 1.78 mmol) in DMSO (1 mL). The resulting thick slurry was filtered and the filtercake was washed with THF (5 mL). The filtrate was concentrated to remove the THF and the remaining hydroxylamine in DMSO was added to Intermediate 5 (193 mg, 0.356 mmol). The reaction mixture was stirred at 75° C. for 2 h. After cooling to room temperature, the reaction mixture was diluted with ethyl acetate and washed three times with water and once with brine. The organic layer was dried over anhydrous MgSO$_4$, filtered, and concentrated, giving 197 mg of product.

ESI-MS calc. for C27H29F7N4O2: 574. Found: 575 (M+H).

INTERMEDIATE 9

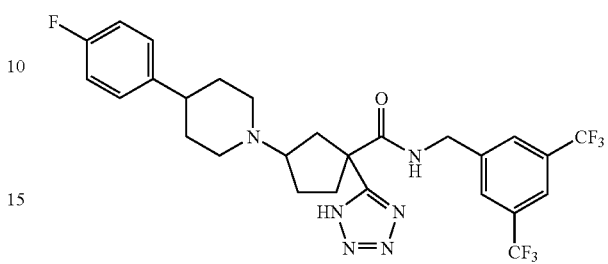

Nitrile Intermediate 5 (331 mg, 0.612 mmol) was combined with sodium azide (239 mg, 3.67 mmol) and triethylamine hydrochloride (253 mg, 1.84 mmol) in 1-methyl-2-pyrrolidinone (9 mL) and stirred at reflux for 4 h. After sitting at room temperature overnight, heating at reflux was continued for 1.5 h. The reaction mixture was diluted with ethyl acetate and washed with water. The aqueous phase was extracted with more ethyl acetate. The combined organic layers were washed with water twice and brine once. The organic layer was dried over anhydrous MgSO$_4$, filtered, and concentrated. Purification by preparative TLC (silica, 20% methanol/DCM) afforded 247 mg of the desired tetrazole (69%).

ESI-MS calc. for C27H27F7N6O: 584. Found: 585 (M+H).

INTERMEDIATE 10

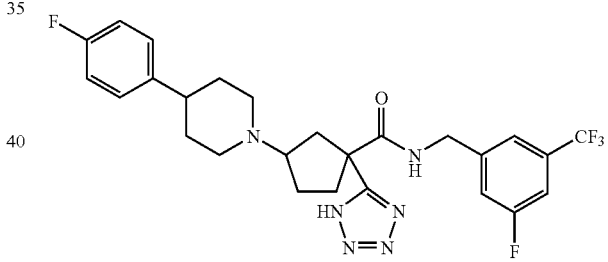

Intermediate 10 was prepared from nitrile Intermediate 6 (179 mg, 0.363 mmol) using the same procedure as detailed for Intermediate 9, resulting in 67.2 mg of the tetrazole product as the cis racemate. ESI-MS calc. for C26H27F5N6O: 534. Found: 535 (M+H).

EXAMPLE 31

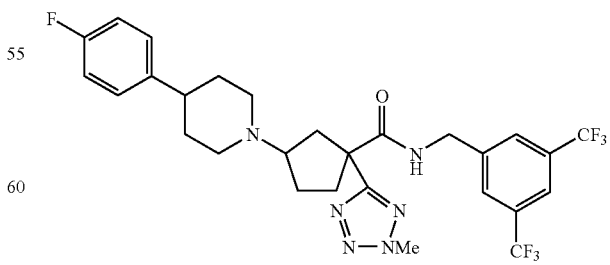

To a solution of tetrazole Intermediate 9, prepared as described above (16.1 mg, 0.0275 mmol), triphenylphosphine (18.1 g, 0.0689 mmol), and methanol (2.8 μL, 0.069 mmol) in DCM (1.5 mL) was added DEAD (12 mg, 11 μL, 0.069 mmol). The resulting mixture was purged with nitrogen and stirred at room temperature for 20 h. Purification by reverse phase HPLC (YMC column) failed to remove the triphenylphosphine oxide form the product. Ion exchange chromatography (sulfonic acid-Varian Mega Bond Elut SCX cartridge: eluting first with 10% methanol/DCM, then with 1:1 2N $NH_3$ in methanol/DCM) afforded the pure methyl tetrazole product. The product was converted to its hydrochloride salt by dissolving in DCM and adding excess 4 N HCl in dioxane, then concentrating, giving 10.6 mg of product salt.

ESI-MS calc. for C28H29F7N6O: 598. Found: 599 (M+H).

EXAMPLE 32

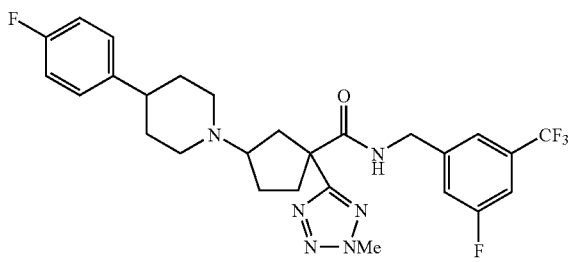

Methyl tetrazole Example 31 was prepared from tetrazole Intermediate 10 (67 mg, 0.13 mmol) using the same procedure as detailed for Example 30, resulting in 43.6 mg of the product as the cis racemate. ESI-MS calc. for C27H29F5N6O: 548. Found: 549 (M+H).

A variety of other alkyl tetrazoles were prepared starting from Intermediate 9 using the same methodology as that detailed in Example 31. The Table below shows some of these amides.

TABLE

OTHER ALKYL TETRAZOLES

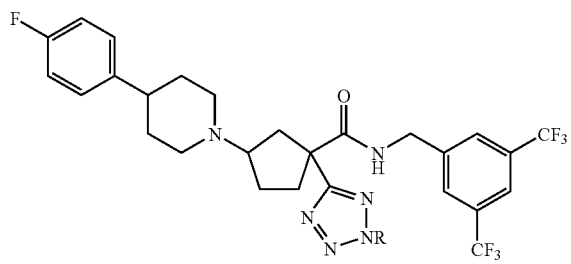

| Ex. | R | MF ESI-MS Found M + 1 |
|---|---|---|
| 32 | CH₂CO₂Me | C30H31F7N6O3 657 |
| 33 | CH₂CH₃ | C29H31F7N6O 613 |
| 34 | CH(CH₃)₂ | C30H33F7N6O 626 |

INTERMEDIATE 11

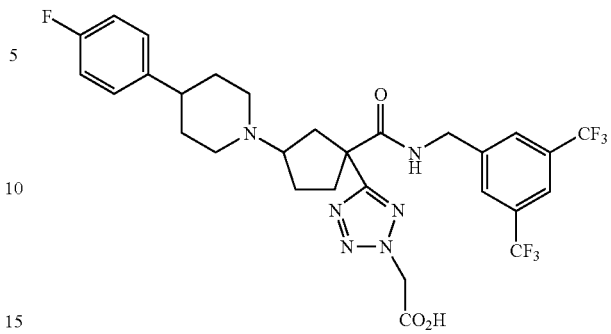

The methyl ester Example 32 (49 mg, 0.075) was dissolved in 1:1 THF/methanol (2 mL) and treated with a solution of LiOH.H₂O (13 mg, 0.30 mmol) in water (1 mL). The reaction mixture was stirred at room temperature for 3 h, then was neutralized with 1 N HCl and concentrated to dryness. The residue was purified by preparative TLC (silica, 20% methanol/DCM) giving 28.7 mg of the carboxylic acid (cis racemate).

ESI-MS calc. for C29H29F7N6O3: 642. Found: 643 (M+H).

EXAMPLE 35

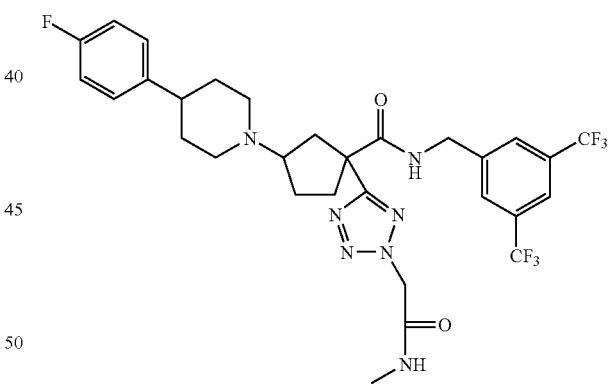

The carboxylic acid Intermediate 11 prepared as described immediately above (3.3 mg, 0.0051 mmol) was combined with EDC (4 mg, 0.02 mmol) and 40% aqueous methylamine (4.4 μL, 0.052 mmol) in DCM (0.5 mL) and stirred for 3 days. The reaction mixture was applied directly to a preparative TLC plate (silica, 0.5/4.5/95 of NH₄OH/methanol/DCM) and after purification gave 2.89 mg of the desired product.

ESI-MS calc. for C30H32F7N7O2: 655. Found: 656 (M+H).

EXAMPLE 36

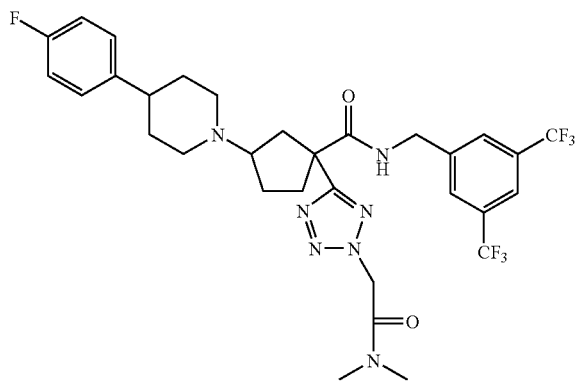

N,N-Dimethylamide analog Example 36 was prepared starting from carboxylic acid Intermediate 11 (3.3 mg, 0.0051 mmol) using the same procedure as detailed in Example 6, giving 3.06 mg of product.

ESI-MS calc. for C31H34F7N7O2: 669. Found: 670 (M+H).

EXAMPLE 37

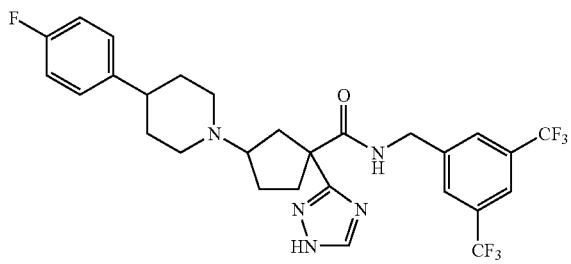

N-[3,5-bis(trifluoromethyl)benzyl]-3-[4-(4-fluorophenyl)piperidin-1-yl]-1-H-1,2,4-triazol-3-yl)cyclopentanecarboxamide The primary amide Intermediate 7 above (97.3 mg, 0.174 mmol) was dissolved in N,N-dimethylformamide dimethylacetal (1.5 mL) and stirred at 120° C. for 3.5 h. After storing at room temperature overnight, the reaction mixture was concentrated and the resulting residue was dissolved in acetic acid (1 mL) and treated with hydrazine hydrate (10.4 mg, 0.209 mmol). The mixture was stirred at 90° C. for 2.5 h, then the solvent was removed under reduced pressure. Purification by reverse phase HPLC (YMC-Pack Pro C18, 100×20 mm ID, 25-100% MeCN/water with 0.1% TFA) and conversion to the HCl salt by repeatedly dissolving in DCM, adding excess 4 N HCl in dioxane, and concentrating, afforded 51.6 mg of the triazole (cis-racemate). ESI-MS calc. for C28H28F7N5O: 583. Found: 584 (M+H).

The above racemate could be separated into two single cis-enantiomers using chiral HPLC (ChiralPak AD column, 10% ethanol/hexane).

EXAMPLE 38

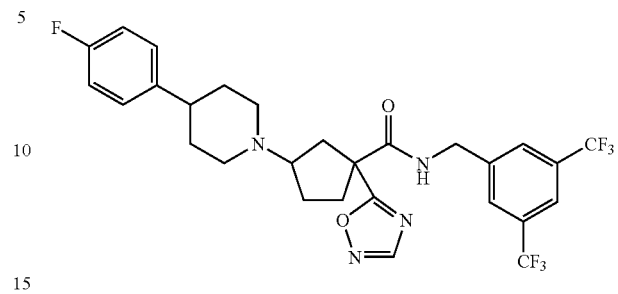

N-[3,5-bis(trifluoromethyl)benzyl]-3-[4-(4-fluorophenyl)piperidin-1-yl]-1-(1,2,4-oxadiazol-5-yl) cyclopentanecarboxamide The primary amide Intermediate 7 above (47 mg, 0.084 mmol) was dissolved in N,N-dimethylformamide dimethylacetal (1.5 mL) and stirred at 120° C. for 3 h. The reaction mixture was concentrated. To the residue was added a premixed solution of hydroxylamine hydrochloride (9 mg, 0.13 mmol), and 5 N NaOH solution (25 µL, 0.13 mmol) in 70% acetic acid/water and the resulting mixture was stirred overnight. Purification by reverse phase HPLC (YMC-Pack Pro C18, 100×20 mm ID, 25-100% MeCN/water with 0.1% TFA), followed by preparative TLC (silica, 10% methanol/DCM) afforded 20.7 mg of oxadiazole (cis-racemate).

ESI-MS calc. for C28H27F7N4O2: 584. Found: 585 (M+H).

EXAMPLE 39

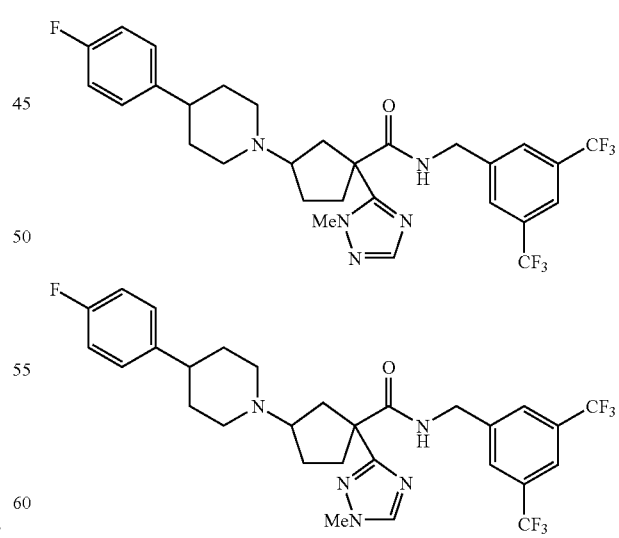

The primary amide Intermediate 7 above (100 mg, 0.179 mmol) was dissolved in N,N-dimethylformamide dimethylacetal (1.5 mL) and stirred at 120° C. for 3 h. After storing at room temperature overnight, the reaction mixture was concentrated and the resulting residue was dissolved in acetic acid (1 mL) and treated with methylhydrazine (12 μL, 0.22 mmol). The reaction mixture was stirred at 90° C. for 3.5 h. Purification by reverse phase HPLC (YMC-Pack Pro C18, 100×20 mm ID, 25-100% MeCN/water with 0.1% TFA), followed by preparative TLC (silica, 0.8/7.2/92 NH$_4$OH/ methanol/DCM) afforded two separated isomers (15.1 mg and 14.2 mg, respectively), both cis-racemates.

ESI-MS calc. for C29H30F7N5O: 597. Found: 598 (M+H).

EXAMPLE 40

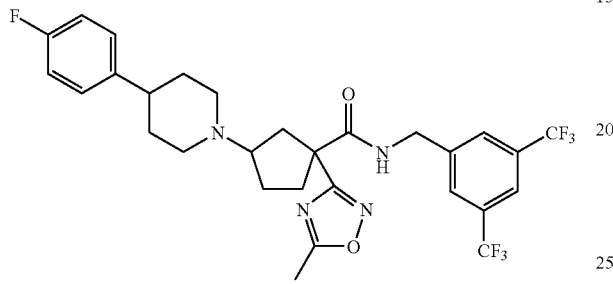

N-[3,5-bis(trifluoromethyl)benzyl]-3-[4-(4-fluorophenyl)piperidin-1-yl]-1-(5-methyl-1,2,4-oxadiazol-3-yl)cyclopentanecarboxamide Intermediate 8 (61.6 mg, 0.107 mmol) was dissolved in acetic anhydride (2 mL) and stirred at reflux for 3 h. The reaction mixture was concentrated. Purification by reverse phase HPLC (YMC-Pack Pro C18, 100×20 mm ID, 25-100% MeCN/water with 0.1% TFA), followed by preparative TLC (silica, Jan. 9, 1990 NH$_4$OH/methanol/DCM, repeated) afforded the product as its free base. Conversion to the HCl salt was accomplished by dissolving in DCM and treating with excess 4 N HCl in dioxane, followed by removal of the solvent, giving 8.34 mg of the product salt (cis-racemate).

ESI-MS calc. for C29H29F7N4O2: 598. Found: 599 (M+H).

EXAMPLE 41

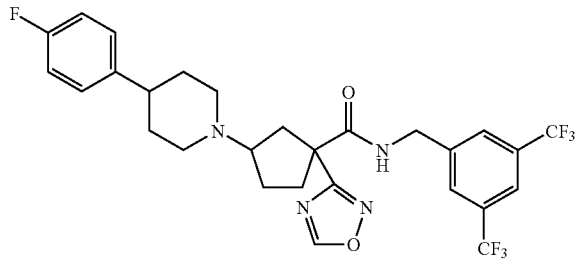

N-[3,5-bis(trifluoromethyl)benzyl]-3-[4-(4-fluorophenyl)piperidin-1-yl]-1-(1,2,4-oxadiazol-3-yl) cyclopentanecarboxamide Intermediate 8 (49.1 mg, 0.0854 mmol) was dissolved in trimethylorthoformate (1 mL), treated with 2 drops of BF$_3$.OEt$_2$, and stirred at room temperature overnight. Since the reaction had not advanced, the reaction was warmed to 90-100° C. and stirred for 33 h. The reaction mixture was concentrated and the residue was purified by preparative TLC (silica, 5% methanol/DCM) to provide 25.2 mg of oxadiazole product. ESI-MS calc. for C28H27F7N4O2: 584. Found: 585 (M+H).

EXAMPLE 42

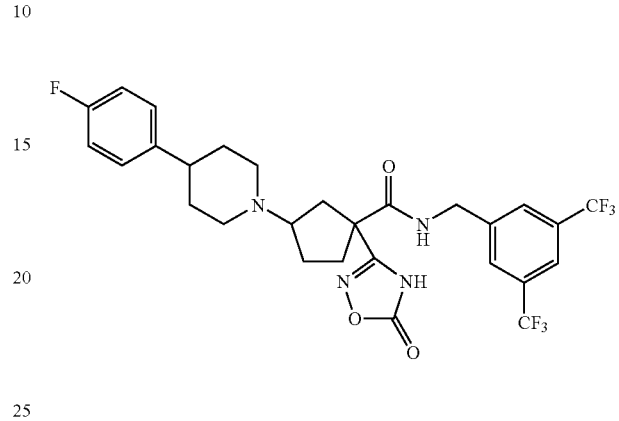

N-[3,5-bis(trifluoromethyl)benzyl]-3-[4-(4-fluorophenyl)piperidin-1-yl]-1-(5-oxo-4,5-dihydro-1,2,4-oxadiazol-3-yl)cyclopentanecarboxamide A solution of Intermediate 8 (79.3 mg, 0.138 mmol) in CHCl$_3$ was treated with triethylamine (25 μL, 0.18 mmol) followed by ethyl chloroformate (14 μL, 0.15 mmol). The reaction mixture was stirred at room temperature for 2 h, then was diluted with DCM and washed with water, followed by brine. The organic layer was dried over anhydrous MgSO$_4$, filtered, and concentrated. To the residue was added m-xylene (2.5 mL) and the resulting solution was stirred at 120° C. for 8 h. The reaction mixture was concentrated and purified by reverse phase HPLC (YMC-Pack Pro C18, 100×20 mm ID, 25-100% MeCN/water with 0.1% TFA), furnishing 19.6 mg of the product as its TFA salt.

ESI-MS calc. for C28H27F7N4O3: 600. Found: 601 (M+H).

EXAMPLE 43

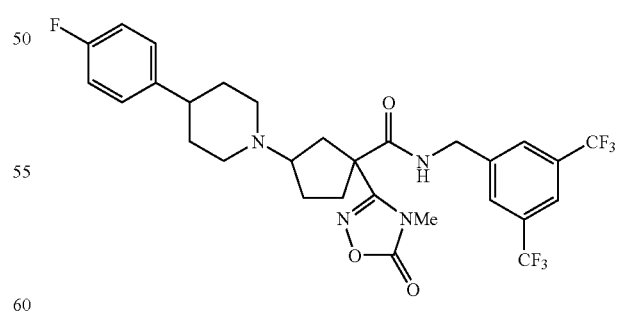

The product oxadiazolone from Example 42 (17.7 mg, 0.0295 mmol) was combined with triphenylphosphine (19.3 mg, 0.0737 mmol), and methanol (3 μL, 0.07 mmol) in DCM (1 mL), and treated under a nitrogen atmosphere with DEAD (12 μL, 0.074 mmol). The reaction mixture was stirred overnight at room temperature. The reaction mixture was applied directly to an ion exchange column (sulfonic acid-Varian Mega Bond Elut SCX cartridge: eluting first with 20% methanol/DCM, then with 1:1 2N NH$_3$ in methanol/DCM), then was further purified by preparative TLC (silica, 10% methanol/DCM) affording the pure methyl oxadiazolone product. The product was converted to its hydrochloride salt (6.1 mg) with 4 N HCl in dioxane (excess) by dissolving and then concentrating.

ESI-MS calc. for C29H29F7N4O3: 614. Found: 615 (M+H).

INTERMEDIATE 12

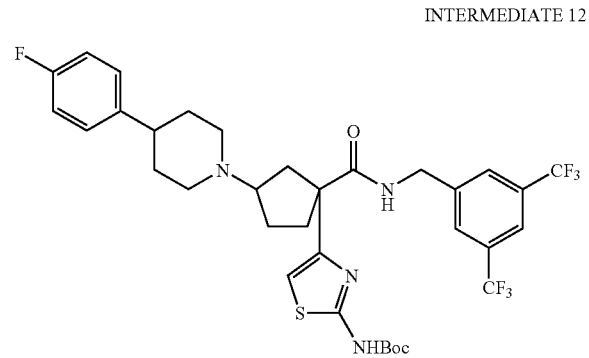

Step A

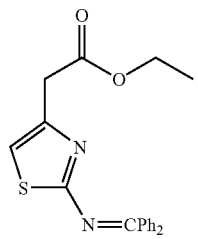

A neat mixture of 54 g (0.29 mole) ethyl(2-aminothiazol-4-yl)acetate and 50 g (0.276 mole) benzophenone imine was stirred at 190° C. for 5 h and then cooled at RT and diluted with 100 mL of CH2Cl2. The entire mixture was transferred onto a silica gel column and eluted with 20% EtOAc/Hexane. The title compound was obtained as light-yellow solid (70 g, 69% yield). $^1$H NMR (300 MHz, CDCl$_3$): δ 1.26 (t, 3H), 3.74 (s, 2H), 4.15 (q, 2H), 6.87 (s, 1H), 77.25-7.86 (m, 10H); Mass Spectrum (NH$_3$—CI): m/z 351 (M+1).

Step B

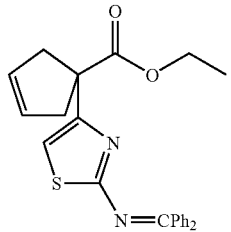

To a mixture of 35 g (0.10 Mole) of the Schiff base ester (Step A above), cis-1,3-dichloro-2-butene (13 mL, 0.11 Mole) in 500 mL of DME at RT was addede in multiple portions solid NaH (60% oil, 10.0 g, 0.25 Mole). The resulting mixture was stirred for 2 days, poured into 2000 mL of ice-water, extracted with 1500 mL of ether. The ether layer was washed with water (3×500 mL), dried over Na2SO4 and evaporated. FC (Silica Gel, 5% EtOAc/Hexane) afforded the title compound as an oil (24 g, 59%). $^1$H NMR (300 MHz, CDCl$_3$): δ 1.20 (t, 3H), 2.87 (d, 2H), 3.19 (d, 2H), 4.14 (q, 2H), 5.29 (s, 2H), 6.71 (s, 1H), 7.26-7.81 (m, 10H). Mass Spectrum (NH$_3$—CI): m/z 403 (M+1).

Step C

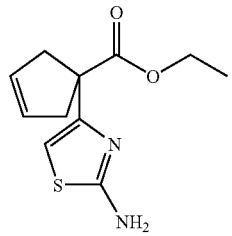

24.0 g (0.059 Mol) of the cyclopentene Schiff base (Step B above) was dissolved in 100 mL of 4N HCl/dioxane. After 1 h, 1.8 mL of water was added. The mixture was stirred for 3 h, evaporated to dryness. The residue was dissolved in 100 mL of CH2Cl2 and added 15 mL of DIEA. The entire mixture was dumped onto a silica gel column, eluted with 20% EtOAc/Hexane to remove benzophenone, then eluted with 40% EtOAc/Hexane to give the title compound as a light yellow solid (12.0 g, 85%). $^1$H NMR (300 MHz, CDCl$_3$): δ 1.19 (t, 3H), 2.79 (d, 12H), 3.15 (d, 2H), 4.13 (q, 2H), 5.66 (s, 2H), 5.82 (wide, 2H), 6.19 (s, 1H).

Step D

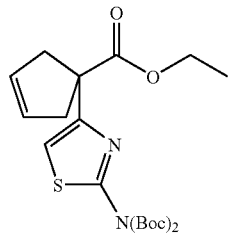

A mixture of 12 g (0.05 Mol) of the aminothiazole (Step C above), 28 g (0.13 Mol) of di-tert-butyl dicarbonate and 0.6 g of DMAP in 250 mL of CH2Cl2 was stirred overnight, and evaporated. The title compound (21.0 g, 96%) was obtained as a yellow oil after FC purification on silica gel (10% EtOAc/Hexane). $^1$H NMR (300 MHz, CDCl$_3$): δ 1.18 (t, 3H), 1.49 (d, 18H), 2.88 (d, 2H), 3.18 (d, 2H), 4.13 (q, 2H), 5.65 (s, 2H), 6.83 (s, 1H). Mass Spectrum (NH$_3$—CI): m/z 439 (M+1).

Step E

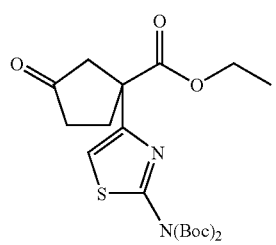

To a solution of 13.1 g (0.03 Mol) of the ester (Step D above) in 50 mL of anhydrous ether at −78° C. was added dropwise a solution of BH3.DMS in THF (14 mL, 0.024 mmol). The cooling bath was removed and the mixture was stirred at RT for 3 h, diluted with 250 mL of CH2Cl2, added 25 g of sodium acetate and 55 g of PCC. The mixture was stirred overnight. The entire mixture was dumped onto a silica gel column and eluted with in 10% EtOAc/Hexane and then 30% EtOAc/Hexane. Two components were obtained. The fast-eluted isomer (yellow oil, 6.0 g) was identified as the title compound. $^1$H NMR (300 MHz, CDCl$_3$): δ 1.21 (t, 3H), 1.50 (s, 18H), 2.33 (t,2H), 2.42-2.70 (m, 2H), 2.78-3.10 (dd, 2H), 4.18 (q, 3H), 6.88 (s, 1H). Mass Spectrum (NH$_3$—CI): m/z 455 (M+1).

Step F

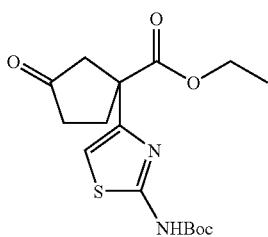

The slow-eluted component from FC in the synthesis of the cyclopentene (Step E above) was proved to be the title compound (gummy material, 1.80 g). $^1$H NMR (300 MHz, CDCl$_3$): δ 1.16 (t, 3H), 1.46 (s, 9H), 2.27 (3, 2H), 2.38-2.62 (m,2H), 2.64-3.00 (dd, 2H), 4.11 (q, 2H), 6.66 (s, 1H). Mass Spectrum (NH$_3$—CI): m/z 355 (M+1).

Step G

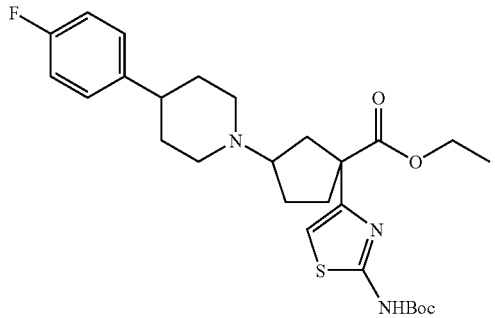

A mixture of 4.54 g (10 mmol) of the keto ester (Step F above), 2.37 g (11 mmol) of 4-fluorophenylpiperidine hydrochloride, 2.60 g (20 mmol) of DIEA, 6.30 g (30 mmol) of sodium triacetoxyborihydride and 5.0 g of molecular seives (4 Å) in 100 mL of CH2Cl2 was stirred overnight, quenched with 50 mL of sat. aq. Na2CO3. The solid was removed by filtration and washing with CH2Cl2. Organic phase was separated, washed with sat. aq. NaHCO3 and dried with Na2SO$_4$, evaporated. The title compound (4.50 g) was obtained as a crude mixture of cis and trans isomers, which was directly used for further hydrolysis without purification. Mass Spectrum (NH$_3$-CD: m/z 618 (M+1).

Step H

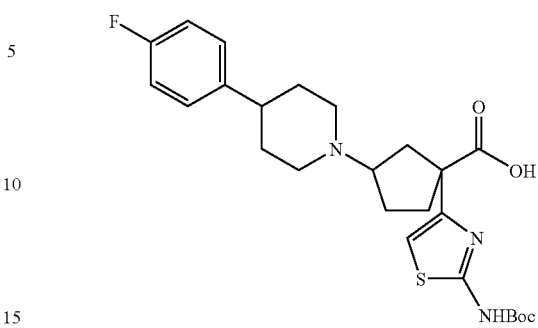

A mixture of 4.50 g of the crude amino ester (Step G above) and 0.82 g (12.6 mmol) of lithium hydroxide monohydrate in a solution of 500 mL of EtOH/H2O (9/1 v/v) was refluxed for 3 h. After evaporation, the residue was chromatographed on silica gel (eluted with 10% MeOH/DCM). Two components were obtained. The fast eluted component (1.80 g) was proposed to be the title compound (1,3-cis isomer, yellow solid, internal salt formation). $^1$H NMR (400 MHz, CDCl$_3$): δ 1.54 (s, 9H), 1.75-2.90 (m, 12H), 3.18 (m, 2H), 3.70 (m, 2H), 6.68 (s, 1H), 6.85-7.10 (m, 4H). Mass Spectrum (NH$_3$—CI): m/z 490 (M+1).

Step I

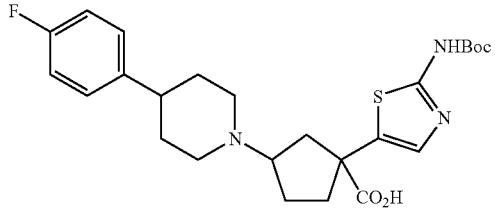

The slow-eluted component (1.90 g) from the step H above was proposed to be the title compound (1,3-trans amino acid, yellow solid). $^1$H NMR (400 MHz, CDCl$_3$): δ 1.49 (s, 9H), 1.20-2.65 (m, 12H), 2.82 (m, 2H), 3.40 (m, 2H), 6.60 (s, 1H), 6.80-7.20 (m, 4H). Mass Spectrum (NH$_3$—CI): m/z 490 (M+1).

Step J

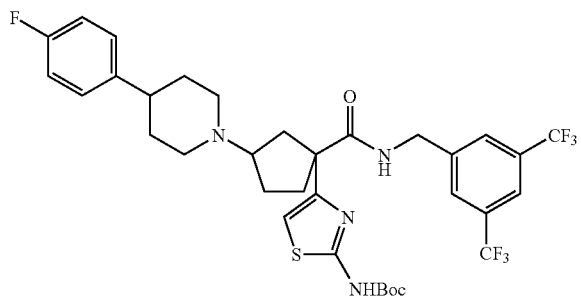

A mixture of 0.300 g (0.6 mmol) of (1,3-cis)-amino acid (Step H above), 0.280 g (1.0 mmol) of 3,5-bis-trifluoromethylbenzylamine hydrochloride and 0.300 g EDC (1.5 mmol) in 5 mL of CH2Cl2 was stirred for 3 h. The reaction mixture was purified on preparative TLC (1000 micron, 10%[aq. NH4OH/MeOH 1/9]/DCM). The title compound (0.250 g) was obtained as a white solid. $^1$H NMR (400 MHz, CDCl$_3$): δ 1.56 (s, 9H), 1.60-2.30 (m, 9H), 2.50 (m, 4H), 2.75(m, 1H), 3.18 (m, 2H), 4.50 (m, 2H), 6.75 (s, 1H), 6.98 (m, 2H), 7.15 (m, 2H), 7.59 (s, 2H), 7.74 (s, 1H), 8.33 (broad, 1H). Mass Spectrum (NH$_3$—CI): m/z 715 (M+1).

The racemic mixture of cis-isomers prepared as described in Intermediate 12, Step J could be resolved into two pure single isomers by chiral HPLC (ChiralPak OD and AD columns).

EXAMPLE 44

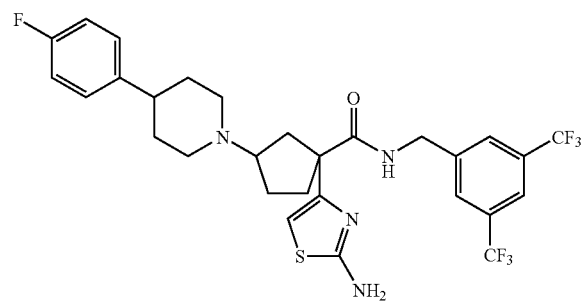

1-(2-amino-1,3-thiazol-4-yl)-N-[3,5-bis(trifluoromethyl)benzyl]-3-[4-(4-fluorophenyl)piperidin-1-yl]cyclopentanecarboxamide A mixture of 0.25 g of the Intermediate 12 in 5 mL of TFA was stirred for 30 min, evaporated and dried in vacuo. The residue was purified on preparative TLC (1000 micron, 10% [aq. NH4OH/MeOH 1/9]/DCM). The title compound (0.220 g) was obtained as a white solid. δ 1.32-2.30 (m, 9H), 2.25 (m, 4H), 2.80 (m, 1H), 3.18 (m, 2H), 4.56 (m, 2H), 5.10 (broad, 2H), 6.38 (s, 1H), 6.98 (m, 2H), 7.28 (m, 2H), 7.45 (t, 1H), 7.64 (s, 2H), 7.75 (s, 1H). Mass Spectrum (NH$_3$—CI): m/z 615 (M+1).

EXAMPLE 45

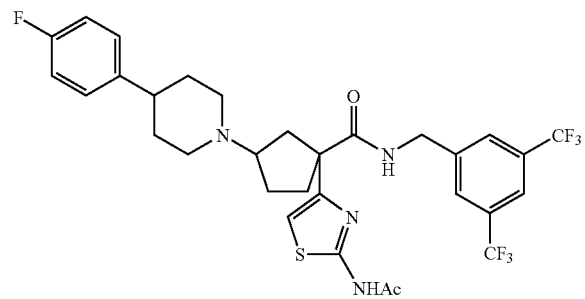

1-[2-(acetylamino)-1,3-thiazol-4-yl]-N-[3,5-bis(trifluoromethyl)benzyl]-3-[4-(4-fluorophenyl)piperidin-1-yl]cyclopentanecarboxamide A mixture of 0.040 g of the compound from EXAMPLE 44, 0.20 g of acetic anhydride and 0.40 g of pyridine in 1.0 mL of CH2Cl2 was stirred overnight, evaporated and dried in vacuo. The residue was purified by preparative TLC (10% [aq. NH4OH/MeOH 1/9]/CH2Cl2). The title compound (0.037 g) was obtained as a white solid. $^1$H NMR (400 MHz, CDCl$_3$): δ 1.60-2.24 (m, 9H), 2.27(s, 3H), 2.50 (m, 4H), 2.85 (m, 1H), 3.20 (m, 2H), 4.55 (m, 2H), 6.83 (s, 1H), 6.97-7.20 (m,5H), 7.64 (s,2H), 7.76 (s, 1H), 9.06 (broad, 1H). LC-MS: m/z 657 (M+1).

EXAMPLE 46

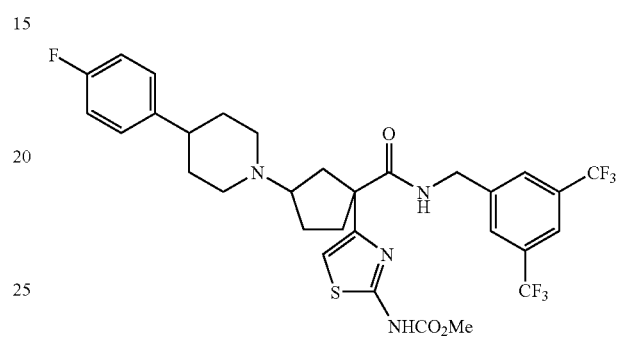

A mixture of 0.013 g of the compound from EXAMPLE 44, 0.100 g of methyl chloroformate and 0.200 g of pyridine in 1.0 mL of CH2Cl2 was stirred overnight, evaporated and dried in vacuo. The residue was purified by preparative TLC (10% [aq. NH4OH/MeOH 1/9]/CH2Cl2). The title compound (0.006 g) was obtained as a white solid. $^1$H NMR (400 MHz, CDCl$_3$): δ 1.95-3.20 (m, 12H), 3.70(m, 2H), 3.82 (s, 3H), 4.55 (m, 2H), 6.95 (m, 3H), 7.20 (m, 2H), 7.53 (broad, 1H), 7.58 (s,2H), 7.68 (s,1H), 8.85 (broad, 1H). LC-MS: m/z 673 (M+1).

EXAMPLE 47

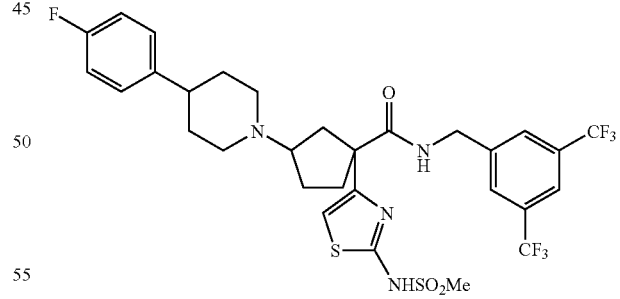

A mixture of 0.040 g of the compound from EXAMPLE 44, 0.400 g of methylsulfonyl anhydride and 0.100 g of pyridine in 1.0 mL of CH2Cl2 was stirred overnight, evaporated and dried in vacuo. The residue was purified by preparative TLC (10% [aq. NH4OH/MeOH 1/9]/CH2Cl2). The title compound (0.009 g) was obtained as a white solid. $^1$H NMR (400 MHz, CDCl$_3$): δ 1.70-3.60 (m, 19H), 4.40(m, 2H), 6.27 (s, 1H), 6.90-7.20 (m, 5H), 7.57 (s, 2H), 7.68 (s, 1H), 8.07 (broad, 1H). LC-MS: m/z 693 (M+1).

EXAMPLE 48

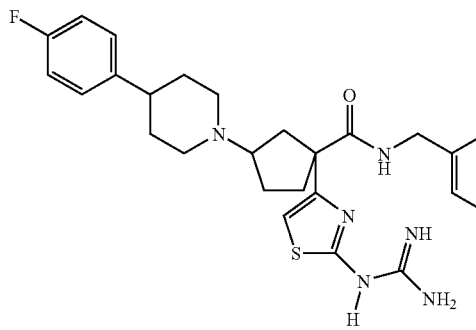

A mixture of 0.122 g of the compound from EXAMPLE 44, 0.400 g of 1H-pyrazole-1-carboxamidine hydrochloride in 5 mL of 4-nitrobenzene in a pressure tube was stirred at 220° C. in sand bath for 1 h. The mixture was directly loaded on preparative TLC and developed with 10% [aq. NH4OH/MeOH 1/9]/CH-2Cl2. The title compound (0.047 g) was obtained as a brown solid. $^1$H NMR (400 MHz, CDCl$_3$): δ 1.60-2.58 (m, 13H), 2.80(m, 1H), 3.18 (m, 2H), 4.50 (m, 2H), 6.52 (s, 1H), 6.87-7.20 (m, 5H), 7.62 (s, 2H), 7.75 (s, 1H). LC-MS: m/z 657 (M+1).

EXAMPLE 49

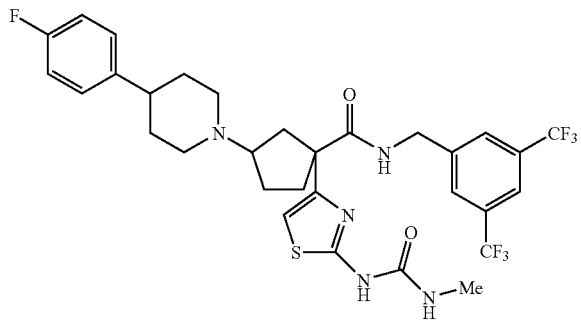

A mixture of 0.031 g of the compound from EXAMPLE 44 and 0.014 g of ethyl isocyanate in 1.0 mL of CH2Cl2 in a vial was heated at 60° C. for two days. The mixture was directly loaded on preparative TLC and developed with 10% [aq. NH4OH/MeOH 1/9]/CH2Cl2. Two components was obtained. The title compound (more polar on TLC, 0.012 g) was obtained as a white solid. $^1$H NMR (400 MHz, CDCl$_3$): δ 1.15 (t, 3H), 1.50-2.50 (m, 14H), 2.80 (m, 1H), 3.17 (m, 2H), 3.30 (q, 2H), 4.52 (m, 2H), 6.65 (s, 1H), 6.98 (m, 2H), 7.10 (m, 2H), 7.18 (m, 1H), 7.67 (s, 2H), 7.74 (s, 1H). 8.98 (broad, 1H). LC-MS: m/z 686 (M+1). The less polar component (10 mg) was identified as overreacted urea. LC-MS: m/z 757 (M+1).

INTERMEDIATE 13

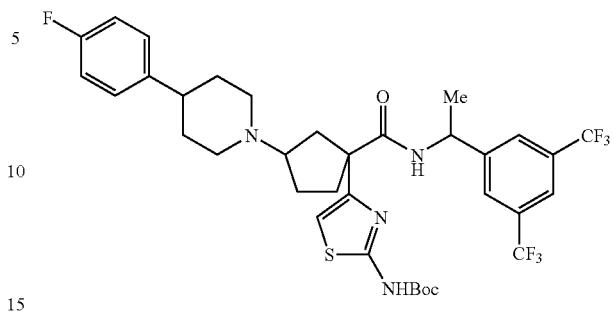

A mixture of 0.200 g (0.6 mmol) of (1,3-cis)-amino acid (Intermediate 12, Step H), 0.150 g (1.0 mmol) of 3,5-bis-trifluoromethylphenylethylamine hydrochloride (Intermediate 2) and 0.380 g EDC (2.0 mmol) in 5 mL of CH2Cl2 was stirred for 3 h. The reaction mixture was purified on preparative TLC (1000 micron, 10%[aq. NH4OH/MeOH 1/9]/DCM). Two components were obtained. Less polar compound (0.094 g): $^1$H NMR (400 MHz, CDCl$_3$): δ 1.47(d, 3H), 1.57 (s, 9H), 1.60-2.00 (m, 7H), 2.05-2.20 (m, 3H), 2.38 (m, 1H), 2.55 (m, 3H), 2.80 (m, 1H), 3.18 (m, 2H), 5.12 (m, 1H), 6.73 (s, 1H), 6.98 (t, 2H), 7.01 (d, 1H), 7.17 (m, 2H), 7.60 (s, 2H), 7.73 (s, 1H), 7.92 (broad, 1H). Mass Spectrum (NH$_3$—Cl): m/z 729 (M+1). More polar compound (0.073 g): $^1$H NMR (400 MHz, CDCl$_3$) δ 1.44(d, 3H), 1.56 (s, 9H), 1.60-2.10 (m, 8H), 2.15 (m, 1H), 2.40 (m, 5H), 2.72 (m, 1H), 3.17 (m, 2H), 5.12 (m, 1H), 6.73 (s, 1H), 6.97 (m, 2H), 7.07 (d, 1H), 7.16 (m, 2H), 7.63 (s, 2H), 7.74 (s, 1H). Mass Spectrum (NH$_3$—Cl): m/z 729 (M+1).

EXAMPLE 50

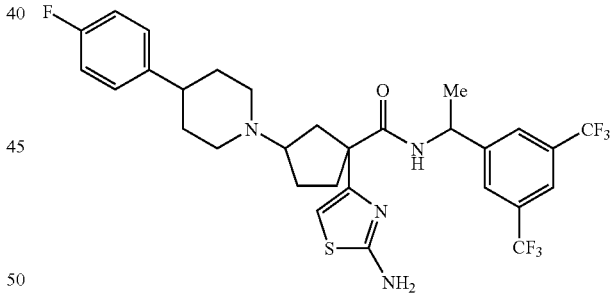

1-(2-amino-1,3-thiazol-4-yl)-N-{1-[3,5-bis(trifluoromethyl)phenyl]ethyl}-3-[4-(4-fluorophenyl)piperidin-1-yl]cyclopentanecarboxamide A mixture of 0.073 g of INTERMEDIATE 13 in 1.5 mL of TFA was stirred for 30 min, evaporated and dried in vacuo. The residue was purified on preparative TLC (1000 micron, 10%[aq. NH4OH/MeOH 1/9]/DCM). From less polar EXAMPLE 50a: the title compound (0.060 g) was obtained as a white solid. $^1$H NMR (400 MHz, CDCl$_3$): δ 1.48 (d, 3H), 1.70-2.00 (m, 7H), 2.00-2.20 (m, 2H), 2.35 (m, 1H), 2.55 (m, 3H), 2.82 (m, 1H), 3.18 (m, 2H), 5.03 (s, 2H), 5.11 (m, 1H), 6.34 (s, 1H), 6.98 (t, 2H), 7.19 (dd, 2H), 7.37 (d, 1H), 7.63 (s, 2H), 7.73 (s, 1H). Mass Spectrum (NH$_3$—Cl): m/z 629

(M+1). From more polar EXAMPLE 50b: the title compound (0.057 g) was obtained as a white solid. $^1$H NMR (400 MHz, CDCl$_3$): δ 1.48 (d, 3H), 1.60-2.30 (m, 10H), 2.35-2.55 (m, 4H), 2.83 (m, 1H), 3.18 (m, 2H), 5.00 (s, 2H), 5.11 (m, 1H), 6.36 (s, 1H), 6.98 (t, 2H), 7.18 (dd, 2H), 7.47 (d, 1H), 7.66 (s, 2H), 7.74 (s, 1H). Mass Spectrum (NH$_3$—CI): m/z 629 (M+1).

EXAMPLE 51

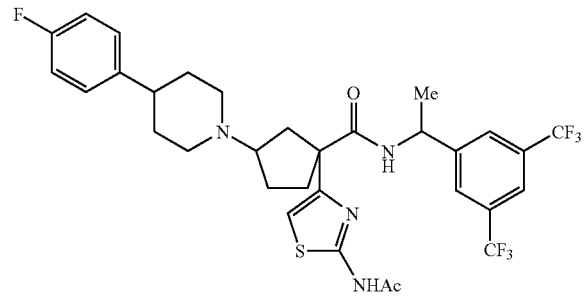

1-[2-(acetylamino)-1,3-thiazol-4-yl]-N-{1-[3,5-bis (trifluoromethyl)phenyl]ethyl}-3-[4-(4-fluorophenyl) piperidin-1-yl]cyclopentanecarboxamide A mixture of 0.020 g of INTERMEDIATE 13, 0.20 g of acetic anhydride and 0.40 g. of pyridine in 1.0 mL of CH2Cl2 was stirred overnight, evaporated and dried in vacuo. The residue was purified by preparative TLC (10% [aq. NH4OH/MeOH 1/9]/CH2Cl2). From less polar EXAMPLE 51a, the title compound (0.018 g) was obtained as a white solid. $^1$H NMR (400 MHz, CDCl$_3$): δ 1.47 (d, 3H), 1.80-2.20 (m, 7H), 2.28(s, 3H), 2.40-2.80 (m, 6H), 3.28 (m, 1H), 3.44 (m, 2H), 5.12 (m, 1H), 6.15 (broad, 1H), 6.76 (s, 1H), 7.00 (m,3H), 7.16 (m, 2H), 7.63 (s, 2H), 7.73 (s, 1H). LC-MS: m/z 671 (M+1). From more polar EXAMPLE 51b, the title compound (0.017 g) was obtained as a white solid. $^1$H NMR (400 MHz, CDCl$_3$): δ 1.48 (d, 3H), 1.80-2.10 (m, 7H), 2.30 (s, 3H), 2.20-2.70 (m, 13H), 2.98 (m, 1H), 3.30 (m, 2H), 5.10 (m, 1H), 6.15 (broad, 1H), 6.79 (s, 1H), 6.87 (d, 1H), 6.98 (m,2H), 7.18 (m, 2H), 7.65 (s, 2H), 7.74 (s, 1H). LC-MS: m/z 671 (M+1).

INTERMEDIATE 14

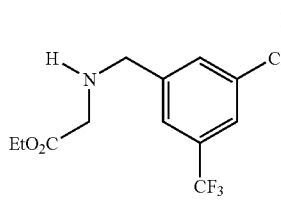

A mixture of 1,3-bis-trifluoromethylbenzaldehyde (4.80 g, 20 mmol), ethyl glycinate hydrochloride (3.0 g, 21 mmol), DIEA (3.0 g, 24 mmol), sodium triacetoxyborihydride (8.4 g, 40 mmol) and molecular sieves (4 Å, 5.0 g) in 100 mL of DCM was stirred overnight, quenched with sat. aq. Na2CO3, filtered and washed with DCM. The filtrates were separated and the organic phase was evaporated. The residue was purified on FC (10% EtOAc/hexane). The title compound (3.5 g) was obtained as a light yellow oil. The HCl salt (4.0 g, white solid) was formed by treatment with 4N HCl/dioxane solution and evaporation. $^1$H NMR (400 MHz, CDCl$_3$): δ 1.27 (t, 3H), 2.10 (broad, 1H), 3.95 (s, 2H), 4.20 (q, 2H), 7.78 (s, 1H), 7.85 (s, 2H).

The following examples were prepared according to the same procedures as those of the Example 44-51 starting from cis amino acids and the corresponding amine intermediates.

| Ex. | R$^1$ | R$^2$ | R$^{10}$ | R$^3$, R$^4$ | R$^5$ | MS: M$^+$ + H$^+$ |
|---|---|---|---|---|---|---|
| 52 | NH$_2$ | 3,5-Bis-CF$_3$-benzyl | H | Ph, H | H | 597.2 |
| 53 | NHAc | 3,5-Bis-CF$_3$-benzyl | H | Ph, H | H | 639.2 |
| 54 | NH$_2$ | 3-F-5-CF$_3$-benzyl | H | Ph, H | H | 547.2 |
| 55 | NHAc | 3-F-5-CF$_3$-benzyl | H | Ph, H | H | 639.2 |
| 56 | NH$_2$ | 3-F-5-CF$_3$-benzyl | H | | Me (indanyl) | 585.2 |
| 57 | NHAc | 3-F-5-CF$_3$-benzyl | H | | Me (indanyl) | 627.2 |
| 58 | NH$_2$ | 3,5-Bis-CF$_3$-benzyl | H | H, H | H | 521.2 |
| 59 | NHAc | 3,5-Bis-CF$_3$-benzyl | H | H, H | H | 563.2 |
| 60 | NHCOPh | 3,5-Bis-CF$_3$-benzyl | H | H, H | H | 625.2 |
| 61 | NHCbz | 3,5-Bis-CF$_3$-benzyl | H | H, H | H | 655.2 |
| 62 | NH$_2$ | 3,5-Bis-CF$_3$-C$_6$H$_4$CHMe | H | H, H | H | 535.2 |
| 63 | NHAc | 3,5-Bis-CF$_3$-C$_6$H$_4$CHMe | H | H, H | H | 577.2 |
| 64 | NH$_2$ | 3,5-Bis-CF$_3$-C$_6$H$_4$CHMe | H | Ph, H | H | 611.2 |
| 65 | NHAc | 3,5-Bis-CF$_3$-C$_6$H$_4$CHMe | H | Ph, H | H | 653.2 |
| 66 | NH$_2$ | 3-CF$_3$-C$_6$H$_5$CHMe | H | | Me (indanyl) | 581.2 |
| 67 | NHAc | 3-CF$_3$-C$_6$H$_5$CHMe | H | | Me (indanyl) | 623.2 |
| 68 | NH$_2$ | 3,5-Bis-CF$_3$-benzyl | Me | Ph, H | H | 611.2 |

-continued

| Ex. | R¹ | R² | R¹⁰ | R³, R⁴ | R⁵ | MS: M⁺ + H⁺ |
|---|---|---|---|---|---|---|
| 69 | NHAc | 3,5-Bis-CF₃-benzyl | Me | Ph, H | H | 653.2 |
| 70 | NHCO₂Me | 3,5-Bis-CF₃-benzyl | Me | Ph, H | H | 669.2 |
| 71 | NH₂ | 3-F-5-CF₃-benzyl | Me | (indanyl, Me) | | 599.2 |
| 72 | NHAc | 3-F-5-CF₃-benzyl | Me | (indanyl, Me) | | 641.2 |
| 73 | NH₂ | 3,5-Bis-CF₃-benzyl | Me | 4-F-Ph, H | H | 629.2 |
| 74 | NHAc | 3,5-Bis-CF₃-benzyl | Me | 4-F-Ph, H | H | 671.2 |
| 75 | NH₂ | 3,5-Bis-CF₃-benzyl | CH₂-CO₂Et | Ph, H | H | 683.2 |
| 76 | NHAc | 3,5-Bis-CF₃-benzyl | CH₂-CO₂Et | Ph, H | H | 725.2 |
| 77 | NH₂ | Benzyl | H | (indanyl, Me) | | 499.2 |
| 78 | NHAc | Benzyl | H | (indanyl, Me) | | 541.2 |
| 79 | NH₂ | (s)-PhCH(CH₂OH)- | H | (indanyl, Me) | | 529 |

EXAMPLE 80

1-[2-(acetylamino)-1,3-thiazol-4-yl]-3-pyrrolidin-1-yN-[3,5-bis(trifluoromethyl)benzyl]cyclopentanecarboxamide Step A A mixture of 1.40 g (4 mmol) of the keto ester (Intermediate 12, Step E) and 0.82 g (12.6 mmol) of lithium hydroxide monohydrate in a solution of 20 ml of MeOH and 2 mL of water was stirred at RT overnight. The entire mixture was poured onto a silica gel column and eluted out with 10% MeOH/CH2Cl2. Evaporation in vacuo afforded a light yellow solid. 1.30 g of the title product was obtained as a fluffy solid. ¹H NMR (300 MHz, CDCl₃): δ 1.52 (t, 9H), 2.10-3.20 (m, 8H), 6.60 (s, 1H).

Step B

A mixture of 0.65 g (2 mmol) of the keto acid (Step A above), 0.70 g (2.5 mmol) of (3,5-bis-trifluoromethyl)benzylamine hydrochloride and 0.95 g EDC (5.0 mmol) in 50 mL of CH2Cl2 was stirred for 2 h. The reaction mixture was diluted with 100 mL of CH2Cl2 and washed with 3N aq. HCl (3×50 ml) and sat. aq. NaHCO3 (50 mL) and water (100 mL), dried over Na2SO4 and evaporated in vacuo. 1.0 g of the title compound was obtained as a yellow solid. ¹H NMR (400 MHz, CDCl₃): δ 1.55 (s, 9H), 2.10-2.22 (m, 2H), 2.38-2.64 (m, 2H), 2.70-3.23 (dd,2H), 4.48-4.64 (m, 2H), 6.74 (s, 1H), 7.36 (broad, 1H), 7.63 (s, 2H), 7.77 (s, 1H), 7.98 (broad, 1H). Mass Spectrum (NH₃—CI): m/z 552 (M+1).

Step C

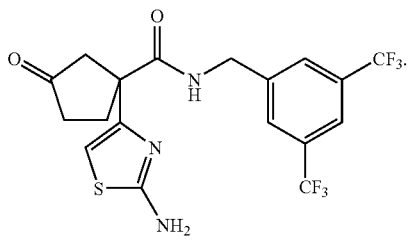

A mixture of 1.10 g (2 mmol) of the Boc compound (Step B above) and 5 mL of neat TFA was stirred at RT for 1 h., evaporated. The residue was dissolved in 50 mL of EtOAc, washed with sat. aq. sodium bicarbonate, dried over Na2SO4, evaporated and dried in vacuum. The title compound (0.85 g, 94%) was obtained as a yellow solid. $^1$H NMR (400 MHz, CDCl$_3$): δ 2.20 (m, 1H), 2.38 (m, 1H), 2.52 (m, 2H), 2.60(d, 1H), 3.18 (d, 1H), 4.58 (m, 2H), 5.34 (broad, 2H), 6.31 (s, 1H), 7.65 (2, 2H), 7.75 (s, 1H), 7.80 (broad, 1H). Mass Spectrum (NH$_3$—CD): m/z 452

Step D

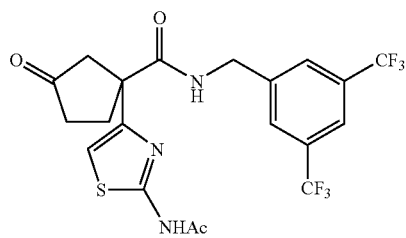

A mixture of 0.85 g (1.89 mmol) of the aminothiazole (Step C above), 0.44 g (5.0 mmol) of acetic anhydride and 0.57 g (3.0 mmol) of pyridine in 20 mL of CH2Cl2 was stirred overnight, diluted with 50 mL of CH2Cl2, washed with water and 2N aq. HCl, dried over Na2SO4 and evaporated. The title compound (0.47 g) was obtained as a light yellow solid after purification on prep TLC (10% MeOH/CH2Cl2. $^1$H NMR (400 MHz, CDCl$_3$): δ 1.00 (m, 2H), 1.18 (m, 2H), 1.70 (m, 1H), 2.28 (m, 1H), 2.50 (m, 2H), 2.70 (m, 1H), 2.80 (d, 1H), 3.28 (d, 1H), 4.55 (m, 2H), 6.80 (s, 1H), 6.98 (broad, 1H), 7.63 (s, 2H), 7.76 (s, 1H), 9.72 (s, 1H). Mass Spectrum (NH$_3$—CI): m/z 520 (M+1).

Step E

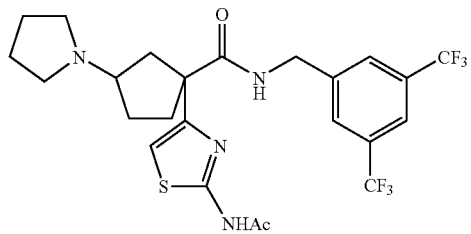

A mixture of 150 mg (0.3 mmol) of the keto amide (Step D above), 100 mg of pyrrolidine, 212 mg (1 mmol) of sodium triacetoxyborihydride and 200 mg of molecular seives (4 Å) in 10 mL of CH2Cl2 was stirred overnight, quenched with 10 mL of sat. aq. Na2CO3. The solid was removed by filtration and washing with CH2Cl2. Organic phase was separated, washed with sat. aq. NaHCO3 and dried with Na2SO4, evaporated. The title compound (127 mg) was obtained as a mixture of cis and trans isomers on preparative TLC (10% [aq. NH4OH/MeOH 1/9]/CH2Cl2). Mass Spectrum (NH$_3$—CI): m/z 549 (M+1).

EXAMPLE 81

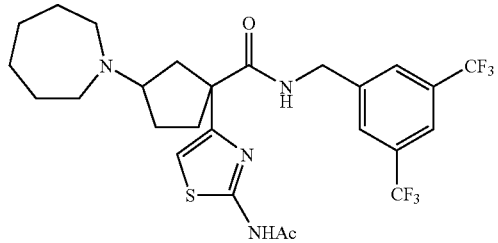

1-[2-(acetylamino)-1,3-thiazol-4-yl]-3-azepan-1-yl-N-[3,5-bis(trifluoromethyl)benzyl]cyclopentanecarboxamide The title compound was prepared as a mixture of 1,3-cis and 1,3-trans diasteromers using the same procedure as detailed in Example 80 (Step D and Step E) with the replacement of pyrrolidine by hexahydrogen-1H-azepine. LC-MS for $C_{26}H_{30}F_6N_4O_2S$ [M$^+$H$^+$] calculated 577.2, found 577.2.

EXAMPLE 82

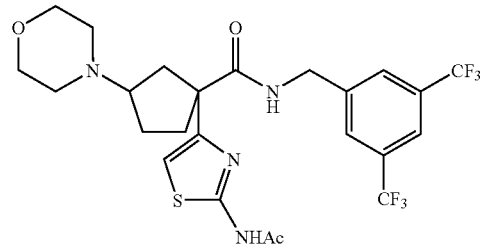

1-[2-(acetylamino)-1,3-thiazol-4-yl]-N-[3,5-bis(trifluoromethyl)benzyl]-3-morpholin-4-ylcyclopentanecarboxamide The title compound was prepared as a mixture of 1,3-cis and 1,3-trans diasteromers using the same procedure as detailed in Example 80 (Step D and Step E) with the replacement of pyrrolidine by morpholine. LC-MS for $C_{24}H_{26}F_6N_4O_3S$ [M$^+$H$^+$] calculated 565.2, found 565.2.

EXAMPLE 83

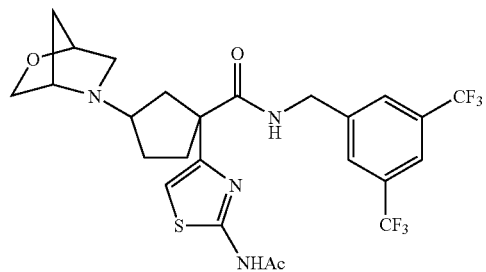

The title compound was prepared as a mixture of 1,3-cis and 1,3-trans diasteromers using the same procedure as detailed in Example 80 (Step D and Step E) with the replacement of pyrrolidine by bicyclic morpholine. LC-MS for $C_{25}H_{26}F_6N_4O_3S$ [M+H+] calculated 577.2, found 577.2.

EXAMPLE 84

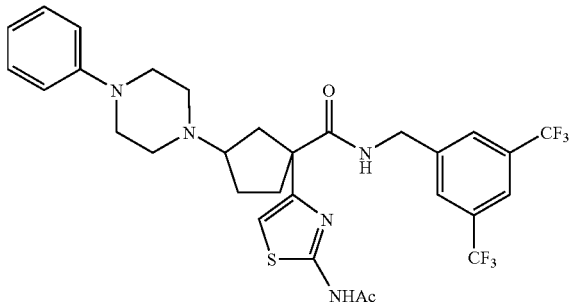

1-[2-(acetylamino)-1,3-thiazol-4-yl]-N-[3,5-bis(trifluoromethyl)benzyl]-3-(4-phenylpiperazin-1-yl)cyclopentanecarboxamide The title compound was prepared as a mixture of 1,3-cis and 1,3-trans diasteromers using the same procedure as detailed in Example 80 (Step D and Step E) with the replacement of pyrrolidine by 4-N-phenylpiperazine. LC-MS for $C_{30}H_{31}F_6N_5O_2S$ [M+H+] calculated 640.2, found 640.2.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

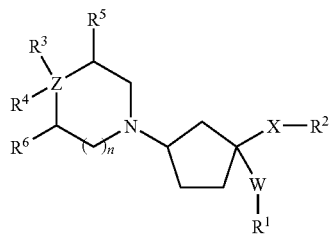

wherein:
X is selected from the group consisting of:
—$NR^{10}$—, —O—, —$CH_2O$—, —$CONR^{10}$—, —$NR^{10}CO$—, —$CO_2$—, —OCO—, —$CH_2NR^{10}$)CO—, —$N(COR^{10})$—, —$CH_2N(COR^{10})$—, phenyl, and $C_{3-6}$ cycloalkyl,
where $R^{10}$ is independently selected from: hydrogen, $C_{1-6}$ alkyl, benzyl, phenyl, and $C_{1-6}$ alkyl-$C_{3-6}$ cycloalkyl, which is unsubstituted or substituted with 1-3 substituents where the substituents are independently selected from: halo, $C_{1-3}$alkyl, $C_{1-3}$alkoxy and trifluoromethyl;
W is selected from:
phenyl and heterocycle, which is unsubstituted or substituted with 1-3 substituents where the substituents are independently selected from: halo, $C_{1-3}$alkoxy and trifluoromethyl;
Z is C;
n is an integer selected from 0, 1, 2, 3 and 4;
$R^1$ is selected from:
(a) halo,
(b) trifluoromethyl,
(c) trifluoromethoxy,
(d) hydroxy,
(e) $C_{1-6}$alkyl,
(f) $C_{3-7}$cycloalkyl,
(g) —O—$C_{1-6}$alkyl,
(h) —O—$C_{3-7}$cycloalkyl,
(i) —$SCF_3$,
(j) —S—$C_{1-6}$alkyl,
(k) —$SO_2$—$C_{1-6}$alkyl,
(l) phenyl,
(m) heterocycle,
(n) —$CO_2R^9$,
(o) —CN,
(p) —$NR^9R^{10}$,
(q) —$NR^9$—$SO_2$—$R^{10}$,
(r) —$SO_2$—$NR^9R^{10}$,
(s) —$CONR^9R^{10}$,
(t) —$NHC(=NH)NR_9R^{10}$,
(u) —NHAc,
(v) —$CH_2C(=O)NHCH_3$,
(w) —$CH_2C(=O)N(CH_3)_2$,
(x) —$NHCO_2CH_3$, and
(y) hydrogen;
$R^9$ is selected from H and $C_{1-3}$alkyl;
$R^2$ is selected from:
($C_{0-6}$alkyl)-phenyl and ($C_{0-6}$alkyl)-heterocycle,
where the alkyl is unsubstituted or substituted with 1-7 substituents where the substituents are independently selected from:
(a) halo,
(b) hydroxy,
(c) —O—$C_{1-3}$alkyl,
(d) trifluoromethyl, and
(e) —$C_{1-3}$alkyl,
and where the phenyl and the heterocycle is unsubstituted or substituted with 1-5 substituents where the substituents are independently selected from:
(a) halo,
(b) trifluoromethyl,
(c) trifluoromethoxy,
(d) hydroxy,
(e) $C_{1-6}$alkyl,
(f) $C_{3-7}$cycloalkyl,
(g) —O—$C_{1-6}$alkyl,
(h) —O—$C_{3-7}$cycloalkyl, (i) —SCF$_3$,
(j) —S—C$_{1-6}$alkyl,
(k) —SO$_2$—C$_{1-6}$alkyl,
(l) phenyl,
(m) heterocycle,
(n) —CO$_2$R$^9$,
(o) —CN,
(p) —NR$^9$R$^{10}$,
(q) —NR$^9$—SO$_2$—R$^{10}$,
(r) —SO$_2$—NR$^9$R$^{10}$, and
(s) —CONR$^9$R$^{10}$;
R$^3$ is —(C$_{0-6}$alkyl)-phenyl,
where the alkyl is unsubstituted or substituted with 1-5 substituents where the substituents are independently selected from:
(a) halo,
(b) hydroxy,
(c) —O—C$_{1-3}$alkyl, and
(d) trifluoromethyl,
and where the phenyl is unsubstituted or substituted with 1-5 substituents where the substituents are independently selected from:
(a) halo,
(b) trifluoromethyl,
(c) hydroxy,
(d) C$_{1-3}$alkyl,
(e) —O—C$_{1-3}$alkyl,
(f) —CO$_2$R$^9$,
(g) —CN,
(h) —NR$^9$R$^{10}$, and
(i) —CONR$^9$R$^{10}$;
R$^4$ is selected from:
(a) hydrogen,
(b) hydroxy,
(c) C$_{1-6}$alkyl,
(d) C$_{1-6}$alkyl-hydroxy,
(e) —O—C$_{1-3}$alkyl,
(f) —CO$_2$R$^9$,
(g) —CONR$^9$R$^{10}$, and
(h) —CN;
or where R$^3$ and R$^4$ may be joined together to form a ring which is selected from:
(a) 1H-indene,
(b) 2,3-dihydro-1H-indene,
(c) 2,3-dihydro-benzofuran,
(d) 1,3-dihydro-isobenzofuran,
(e) 2,3-dihydro-benzothiofuran, and
(f) 1,3-dihydro-isobenzothiofuran,
or where R$^3$ and R$^5$ or R$^4$ and R$^6$ may be joined together to form a ring which is phenyl,
wherein the ring is unsubstituted or substituted with 1-7 substituents where the substituents are independently selected from:
(a) halo,
(b) trifluoromethyl,
(c) hydroxy,
(d) C$_{1-3}$alkyl,
(e) —O—C$_{1-3}$alkyl,
(f) —CO$_2$R$^9$,
(g) —CN,
(h) —NR$^9$R$^{10}$, and
(i) —CONR$^9$R$^{10}$; and
R$^5$ and R$^6$ are independently selected from:
(a) hydrogen,
(b) hydroxy,
(c) C$_{1-6}$alkyl,
(d) C$_{1-6}$alkyl-hydroxy,
(e) —O—C$_{1-3}$alkyl,
(f) oxo, and
(g) halo;
or a pharmaceutically acceptable salt individual diastereomer thereof.

2. The compound of claim 1 of the formula Ia:

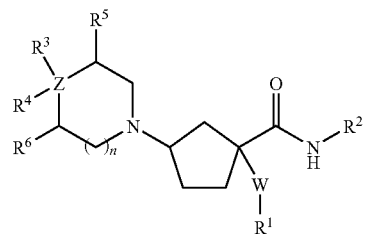

or a pharmaceutically acceptable salt or individual diastereomers thereof.

3. The compound of claim 1 of the formula Ib:

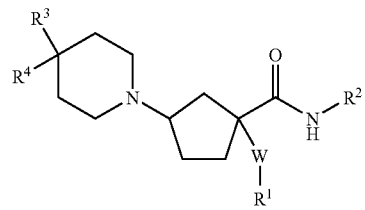

or a pharmaceutically acceptable salt or individual diastereomers thereof.

4. The compound of claim 1 of the formula Ic:

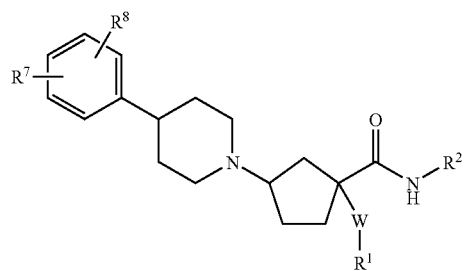

and wherein R$^7$ and R$^8$ are independently selected from:
(a) hydrogen,
(b) halo,
(c) trifluoromethyl,
(d) hydroxy,
(e) C$_{1-3}$alkyl,
(f) —O—C$_{1-13}$alkyl,
(g) —CO$_2$H,
(h) —CO$_2$C$_{1-3}$alkyl, and
(i) —CN;
or a pharmaceutically acceptable salt and individual diastereomers thereof.

5. The compound of claim 1 of the formula Id:

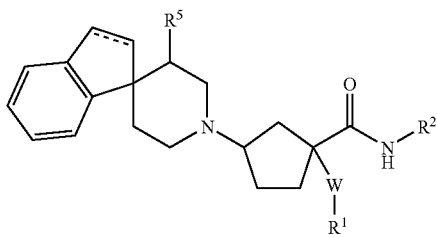

wherein the dash line represents either single or double bonds;
or a pharmaceutically acceptable salt and individual diastereomers thereof.

6. The compound of claim 1 of the formula:

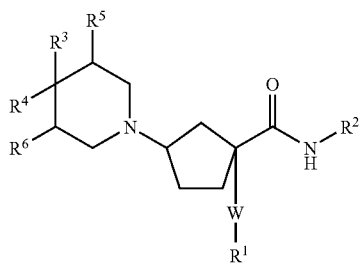

wherein W is selected from furanyl, imidazolyl, oxadiazolyl, oxazolyl, phenyl, pyrazolyl, pyrazinyl, pyridyl, pyridazinyl, pyrimidyl, pyrrolyl, thiadiazolyl, and thiazolyl,
or a pharmaceutically acceptable salt and individual diastereomers thereof.

7. The compound of claim 1 wherein W is selected from furanyl, imidazolyl, oxadiazolyl, oxazolyl, phenyl, pyrazolyl, pyrazinyl, pyridyl, pyridazinyl, pyrimidyl, pyrrolyl, thiadiazolyl, thiazolyl, thienyl, and triazolyl, and N-oxides thereof.

8. The compound of claim 1 wherein X is —CONH—.

9. The compound of claim 1 wherein n is 0 and 1.

10. The compound of claim 1 wherein $R^1$ is selected from:
(a) hydrogen
(b) halo
(c) $C_{1-3}$alkyl,
(d) —O—$C_{1-3}$alkyl,
(e) —$CO_2R^9$,
(f) —S—$C_{1-3}$alkyl,
(g) —$SO_2$—$C_{1-13}$alkyl,
(h) —$SCF_3$,
(i) NHC(=NH)$NR^9R^{10}$
(j) —$NR^9R^{10}$,
(k) —$NR^9$—$SO_2$—$R^{10}$,
(l) —$SO_2$—$NR^9R^{10}$, and
(m) —$CONR^9R^{10}$.

11. The compound of claim 1 wherein $R^2$ is selected from —($C_{0-4}$alkyl)-phenyl and —($C_{0-4}$alkyl)-heterocycle,
where heterocycle is selected from:
furanyl, imidazolyl, oxadiazolyl, oxazolyl, pyrazolyl, pyrazinyl, pyridyl, pyridazinyl, pyrimidyl, pyrrolyl, thiadiazolyl, thiazolyl, thienyl, and triazolyl, and N-oxides thereof,
where the alkyl is unsubstituted or substituted with 1-7 substituents where the substituents are independently selected from:
(a) halo,
(b) hydroxy,
(c) —O—$C_{1-3}$alkyl, and
(d) trifluoromethyl,
and where the phenyl or heterocycle is unsubstituted or substituted with 1-5 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-13}$alkyl,
(g) —$CO_2R^9$,
(h) —S—$C_{1-3}$alkyl,
(i) —$SO_2$—$C_{1-3}$alkyl,
(j) —$SCF_3$,
(k) —$CO_2R^9$,
(l) —$NR^9R^{10}$,
(m) —$NR^9$—$SO_2$—$R^{10}$,
(n) —$O_2$—$NR^9R^{10}$, and
(o) —$CONR^9R^{10}$.

12. The compound of claim 1 wherein $R^2$ is selected from —($C_{0-4}$alkyl)-phenyl and —($C_{0-4}$alkyl)-heterocycle,
where heterocycle is selected from: pyridyl, pyridazinyl, and N-oxides thereof, where the alkyl is unsubstituted or substituted with 1-7 substituents where the substituents are independently selected from:
(a) halo,
(b) hydroxy,
(c) —O—$C_{1-3}$alkyl, and
(d) trifluoromethyl,
and where the phenyl or heterocycle is unsubstituted or substituted with 1-3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2H$,
(i) —S—$C_3$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

13. The compound of claim 1 wherein $R^2$ is selected from —$CH_2$-phenyl and —$CH_2$-heterocycle,
where heterocycle is selected from: pyridyl, pyridazinyl, and N-oxides thereof, and where the phenyl or heterocycle is unsubstituted or substituted with 1-3 substituents where the substituents are independently selected from:
(a) halo,
(b) trifluoromethyl,
(c) trifluoromethoxy,
(d) hydroxy,
(e) $C_{1-3}$alkyl,
(f) —O—$C_{1-3}$alkyl,
(g) —$CO_2$—$C_{1-3}$alkyl,
(h) —$CO_2H$,
(i) —S—$C_{1-3}$alkyl,
(j) —$SO_2$—$C_{1-3}$alkyl,
(k) —$SCF_3$,
(l) —$NH_2$,
(m) —NH—$SO_2$—$C_{1-3}$alkyl, and
(n) —$SO_2$—$NH_2$.

14. The compound of claim 1 wherein $R^2$ is selected from:
(1) —CH$_2$-(phenyl),
(2) —CH$_2$-(4-bromophenyl),
(3) —CH$_2$-(3-chlorophenyl),
(4) —CH$_2$-(3,5-difluorophenyl),
(5) —CH$_2$-((2-trifluoromethyl)phenyl),
(6) —CH$_2$-((3-trifluoromethyl)phenyl),
(7) —CH$_2$-((4-trifluoromethyl)phenyl),
(8) —CH$_2$-((3-trifluoromethoxy)phenyl),
(9) —CH$_2$-((3-trifluoromethylthio)phenyl),
(10) —CH$_2$-((3-trifluoromethoxy-5-thiomethyl)phenyl),
(11) —CH$_2$-((3-trifluoromethoxy-5-methoxy)phenyl),
(12) —CH$_2$-((3-trifluoromethoxy-5-methanesulfonyl) phenyl),
(13) —CH$_2$-((3-trifluoromethoxy-5-amino)phenyl),
(14) —CH$_2$-((3-trifluoromethoxy-5-aminomethanesulfonyl)phenyl),
(15) —CH$_2$-((3-trifluoromethoxy-5-sulfonylamino)phenyl),
(16) —CH$_2$-((3,5-bis-trifluoromethyl)phenyl),
(17) —CH$_2$-((3-fluoro-5-trifluoromethyl)phenyl),
(18) —CH(CH$_3$)-((3,5-bis-trifluoromethyl)phenyl),
(19) —C(CH$_3$)$_2$-((3,5-bis-trifluoromethyl)phenyl),
(20) —CH$_2$-(4-(2-trifluoromethyl)pyridyl),
(21) —CH$_2$-(5-(3-trifluoromethyl)pyridyl),
(22) —CH$_2$-(5-(3-trifluoromethyl)pyridazinyl),
(23) —CH$_2$-(4-(2-trifluoromethyl)pyridyl-N-oxide), and
(24) —CH$_2$-(5-(3-trifluoromethyl)pyridyl-N-oxide).

15. The compound of claim 1 wherein $R^3$ is hydrogen or phenyl, where the phenyl is unsubstituted or substituted with 1-5 substituents where the substituents are independently selected from:
(a) halo,
(b) trifluoromethyl,
(c) hydroxy,
(d) C$_{1-3}$alkyl,
(e) —O—C$_{1-3}$alkyl,
(f) —CO$_2$R$^9$,
(g) —CN,
(h) —NR$^9$R$^{10}$, and
(i) —CONR$^9$R$^{10}$.

16. The compound of claim 1 wherein $R^3$ is hydrogen or phenyl, where the phenyl is unsubstituted or substituted with 1-3 substituents where the substituents are independently selected from:
(a) halo,
(c) hydroxy,
(d) C$_{1-3}$alkyl,
(e) —O—C$_{1-3}$alkyl, and
(f) —CO$_2$R$^9$.

17. The compound of claim 1 wherein $R^3$ is phenyl, or para-fluorophenyl.

18. The compound of claim 1 wherein $R^4$ is selected from:
(a) hydrogen,
(b) hydroxy,
(c) —CO$_2$H,
(d) —CO$_2$C$_{1-6}$alkyl,
(e) —CN.

19. The compound of claim 1 wherein $R^5$ and $R^6$ are independently selected from:
(a) hydrogen,
(b) hydroxy,
(c) —CH$_3$,
(d) —O—CH$_3$, and
(e) oxo.

20. A pharmaceutical composition which comprises an inert carrier and a compound of claim 1.

21. A method for treating, ameliorating or controlling rheumatoid arthritis which comprises administering to a patient in need thereof an effective amount of the compound of claim 1.

22. The compound of claim 1, which is selected from the group consisting of the following compounds, or a pharmaceutically acceptable salt or individual diastereomer thereof:

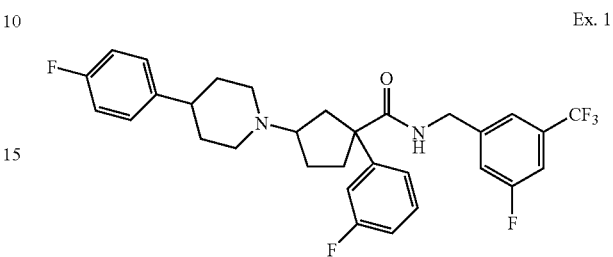

Ex. 1

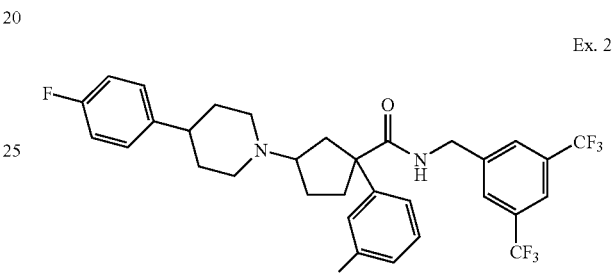

Ex. 2

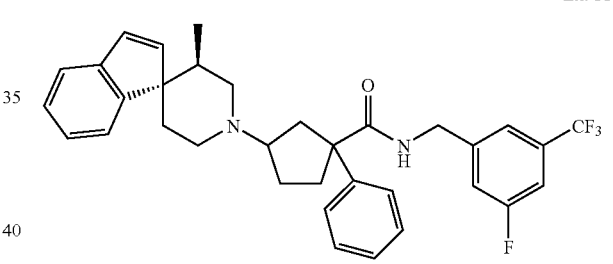

Ex. 11

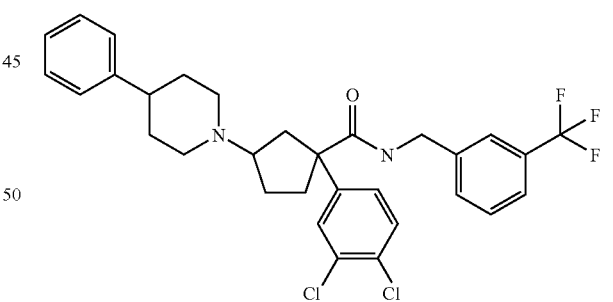

Ex. 24

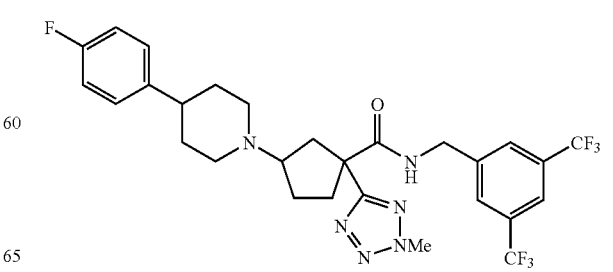

Ex. 31

Ex. 32
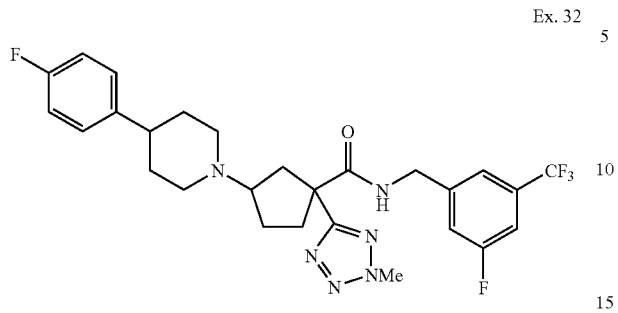
Ex. 35
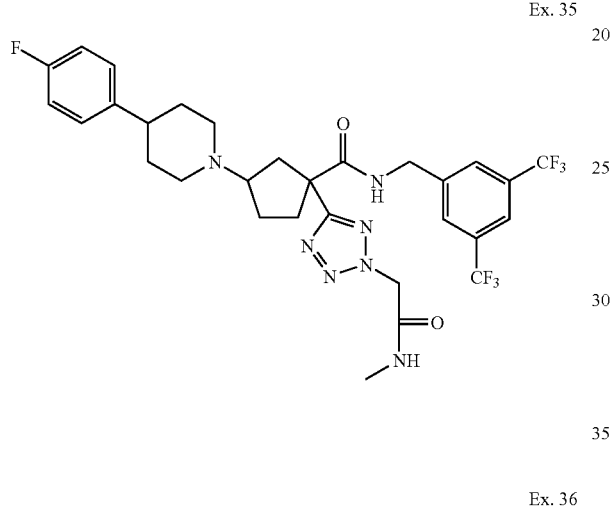
Ex. 36
Ex. 37
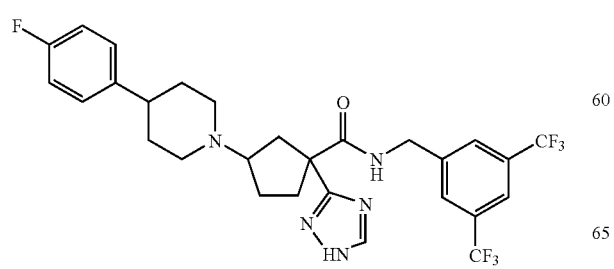
Ex. 38
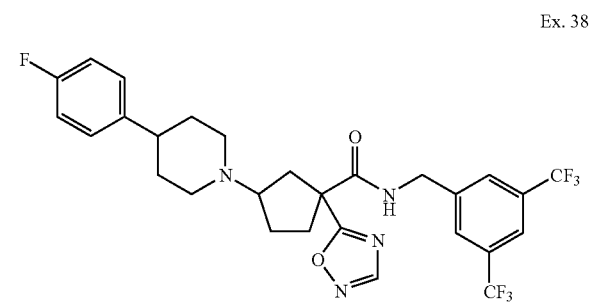
Ex. 39
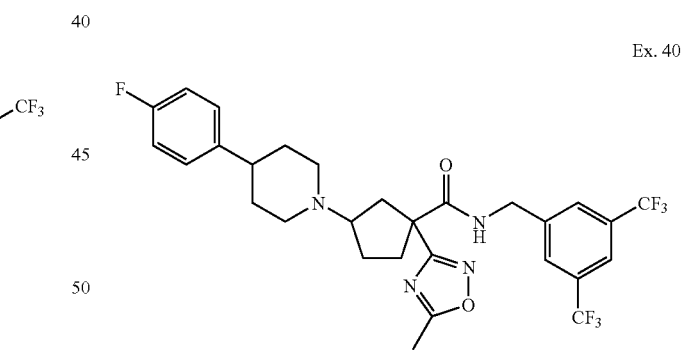
Ex. 40
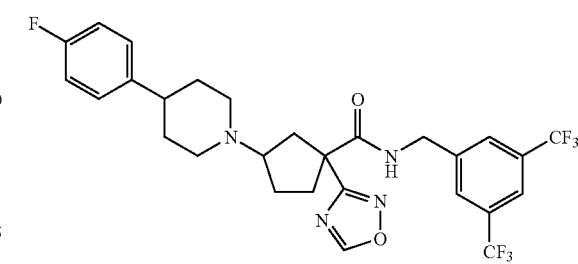
Ex. 41

-continued
Ex. 42
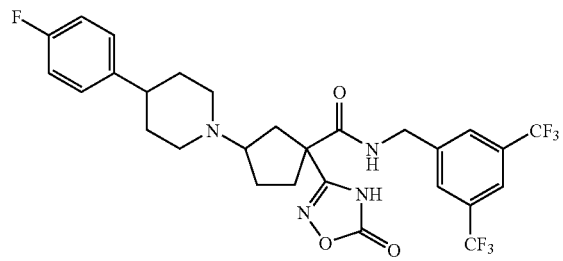
Ex. 43
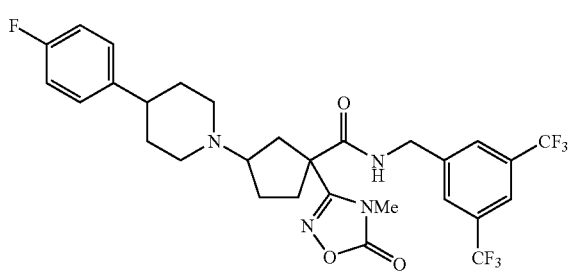
Ex. 44
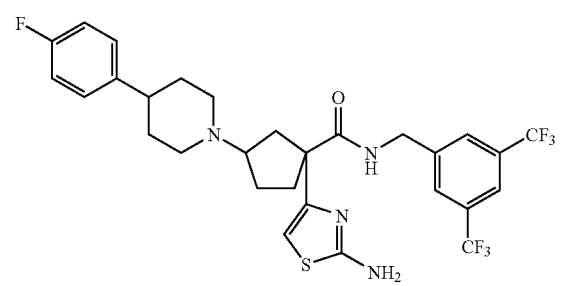
Ex. 45
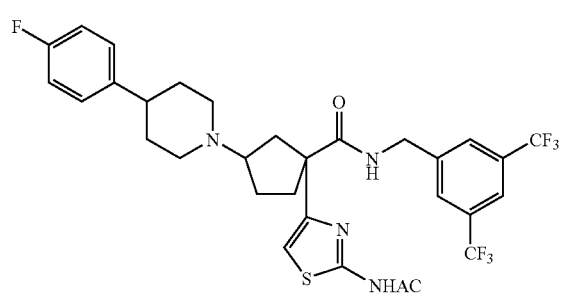
Ex. 46
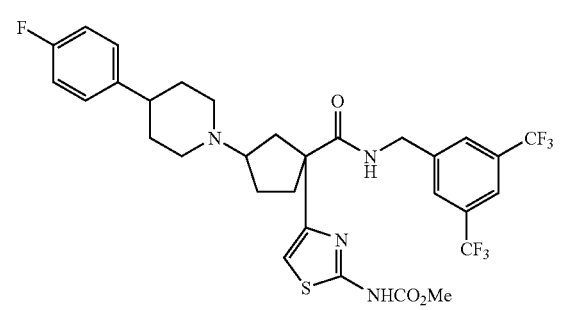
-continued
Ex. 47
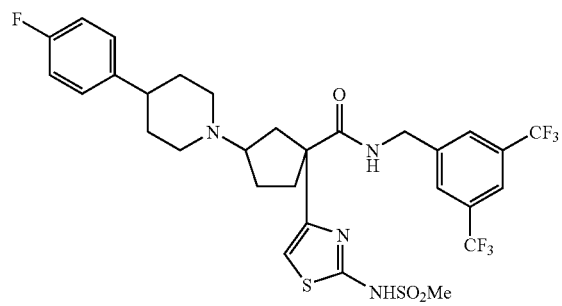
Ex. 48
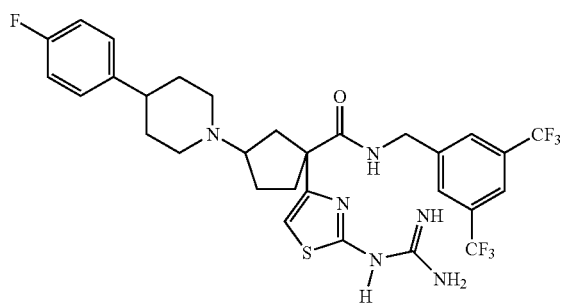
Ex. 49
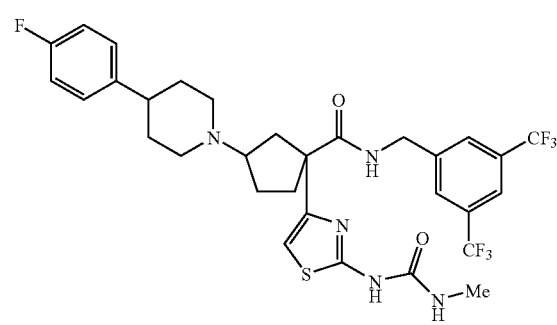
Ex. 50
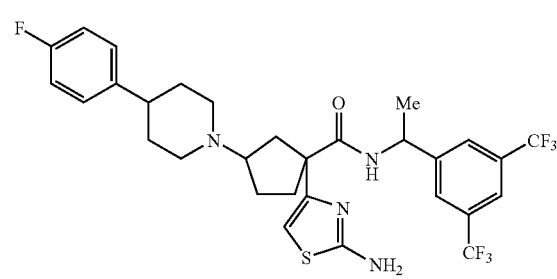
Ex. 51
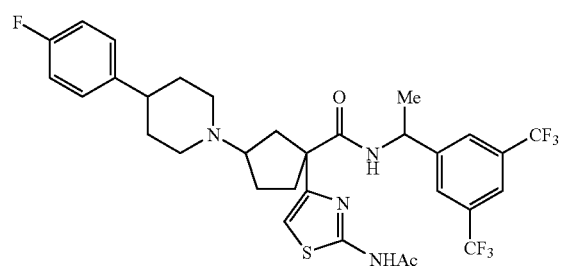

-continued
Ex. 80
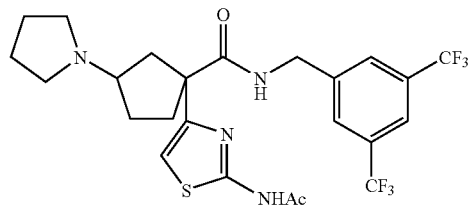
and
-continued
Ex. 81
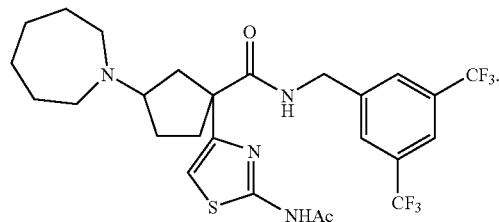
* * * * *